US012779118B2

(12) United States Patent
Stafford

(10) Patent No.: US 12,779,118 B2
(45) Date of Patent: Nov. 3, 2026

(54) FLEXIBLE PATCH FOR FLUID DELIVERY AND MONITORING BODY ANALYTES

(71) Applicant: ABBOTT DIABETES CARE INC., Alameda, CA (US)

(72) Inventor: Gary Ashley Stafford, Hayward, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 524 days.

(21) Appl. No.: 18/215,283

(22) Filed: Jun. 28, 2023

(65) Prior Publication Data

US 2023/0414870 A1 Dec. 28, 2023

Related U.S. Application Data

(63) Continuation of application No. 16/438,556, filed on Jun. 12, 2019, now Pat. No. 11,724,029, which is a (Continued)

(51) Int. Cl.

*A61M 5/172* (2006.01)
*A61B 5/00* (2006.01)
(Continued)

(52) U.S. Cl.

CPC ......... *A61M 5/1723* (2013.01); *A61B 5/0022* (2013.01); *A61B 5/14503* (2013.01); (Continued)

(58) Field of Classification Search

CPC ............ A61M 5/1723; A61M 5/14248; A61M 2005/1726; A61M 2205/3569; (Continued)

(56) References Cited

U.S. PATENT DOCUMENTS 3,123,790 A 3/1964 Tyler
3,211,001 A 10/1965 Petit
(Continued)

FOREIGN PATENT DOCUMENTS

CA 2291105 12/1998
EP 1177802 2/2002
(Continued)

OTHER PUBLICATIONS

U.S. Pat. No. 8,282,549 B2, Brauker et al., published Oct. 9, 2012; 73 pages; Anlage TW 2, Taylor Wessing, Statement of Defence in *Abbott* v. *Dexcom*, Opposition to EP 3782539.
(Continued)

*Primary Examiner* — Navin Natnithithadha
(74) *Attorney, Agent, or Firm* — Sterne, Kessler, Goldstein & Fox P.L.L.C.

(57) ABSTRACT

A wearable, conductive textile patch is provided that may include any of a number of features for monitoring body analytes and/or delivering fluids to a body. In one embodiment of the invention, a single, patch-mounted system monitors glucose levels of a diabetic person and provides appropriate doses of insulin in response to the glucose measurements. A hand-held user interface can be provided for wirelessly controlling the system and/or receiving information from it. Conductive pathways can be formed in the fabric of the patch. Components that can be integrated into the flexible patch include a power source, controller, transmitter, antenna, temperature and other sensors, fluid pump, infusion set, electrical pathways, switches, controls, electrodes, connectors, resistors and other circuit elements. Such components can be embedded, interwoven or coated on to the flexible patch instead of or in addition to surface mounting. Methods associated with use of the flexible patch system are also covered.

18 Claims, 2 Drawing Sheets

Related U.S. Application Data continuation of application No. 14/989,548, filed on Jan. 6, 2016, now Pat. No. 10,363,363, which is a continuation of application No. 11/552,065, filed on Oct. 23, 2006, now Pat. No. 9,259,175.

(51) Int. Cl.
*A61B 5/145* (2006.01)
*A61M 5/142* (2006.01)

(52) U.S. Cl.
CPC ........ *A61B 5/14532* (2013.01); *A61B 5/6833* (2013.01); *A61M 5/14248* (2013.01); *A61B 2560/0252* (2013.01); *A61B 2560/0412* (2013.01); *A61M 2005/1726* (2013.01); *A61M 2205/3569* (2013.01); *A61M 2205/3592* (2013.01); *A61M 2205/82* (2013.01); *A61M 2230/005* (2013.01); *A61M 2230/201* (2013.01); *A61M 2230/50* (2013.01)

(58) Field of Classification Search
CPC ...... A61M 2205/3592; A61M 2205/82; A61M 2230/005; A61M 2230/201; A61M 2230/50; A61B 5/0022; A61B 5/14503; A61B 5/14532; A61B 5/6833; A61B 2560/0252; A61B 2560/0412
See application file for complete search history.

(56) References Cited

U.S. PATENT DOCUMENTS 3,260,656 A 7/1966 Ross, Jr.
3,581,062 A 5/1971 Aston
3,653,841 A 4/1972 Klein
3,719,564 A 3/1973 Lilly, Jr. et al.
3,776,832 A 12/1973 Oswin et al.
3,837,339 A 9/1974 Aisenberg et al.
3,926,760 A 12/1975 Allen et al.
3,949,388 A 4/1976 Fuller
3,972,320 A 8/1976 Kalman
3,979,274 A 9/1976 Newman
4,008,717 A 2/1977 Kowarski
4,016,866 A 4/1977 Lawton
4,036,749 A 7/1977 Anderson
4,055,175 A 10/1977 Clemens et al.
4,059,406 A 11/1977 Fleet
4,076,596 A 2/1978 Connery et al.
4,098,574 A 7/1978 Dappen
4,100,048 A 7/1978 Pompei et al.
4,120,292 A 10/1978 LeBlanc, Jr. et al.
4,129,128 A 12/1978 McFarlane
4,151,845 A 5/1979 Clemens
4,168,205 A 9/1979 Danninger et al.
4,172,770 A 10/1979 Semersky et al.
4,178,916 A 12/1979 McNamara
4,206,755 A 6/1980 Klein
4,224,125 A 9/1980 Nakamura et al.
4,240,438 A 12/1980 Updike et al.
4,245,634 A 1/1981 Albisser et al.
4,247,297 A 1/1981 Berti et al.
4,294,258 A 10/1981 Bernard
4,327,725 A 5/1982 Cortese et al.
4,340,458 A 7/1982 Lerner et al.
4,344,438 A 8/1982 Schultz
4,349,728 A 9/1982 Phillips et al.
4,352,960 A 10/1982 Dormer et al.
4,356,074 A 10/1982 Johnson
4,365,637 A 12/1982 Johnson
4,366,033 A 12/1982 Richter et al.
4,373,527 A 2/1983 Fischell
4,375,399 A 3/1983 Havas et al.
4,384,586 A 5/1983 Christiansen
4,390,621 A 6/1983 Bauer
4,401,122 A 8/1983 Clark, Jr.
4,404,066 A 9/1983 Johnson
4,418,148 A 11/1983 Oberhardt
4,425,920 A 1/1984 Bourland et al.
4,427,770 A 1/1984 Chen et al.
4,431,004 A 2/1984 Bessman et al.
4,436,094 A 3/1984 Cerami
4,440,175 A 4/1984 Wilkins
4,441,968 A 4/1984 Emmer et al.
4,450,842 A 5/1984 Zick et al.
4,458,686 A 7/1984 Clark, Jr.
4,461,691 A 7/1984 Frank
4,469,110 A 9/1984 Slama
4,477,314 A 10/1984 Richter et al.
4,478,976 A 10/1984 Goertz et al.
4,484,987 A 11/1984 Gough
4,494,950 A 1/1985 Fischell
4,509,531 A 4/1985 Ward
4,522,690 A 6/1985 Venkatasetty
4,524,114 A 6/1985 Samuels et al.
4,526,661 A 7/1985 Steckhan et al.
4,527,240 A 7/1985 Kvitash
4,534,356 A 8/1985 Papadakis
4,538,616 A 9/1985 Rogoff
4,543,955 A 10/1985 Schroeppel
4,545,382 A 10/1985 Higgins et al.
4,552,840 A 11/1985 Riffer
4,560,534 A 12/1985 Kung et al.
4,571,292 A 2/1986 Liu et al.
4,573,994 A 3/1986 Fischell et al.
4,581,336 A 4/1986 Malloy et al.
4,595,011 A 6/1986 Phillips
4,619,754 A 10/1986 Niki et al.
4,619,793 A 10/1986 Lee
4,627,445 A 12/1986 Garcia et al.
4,627,908 A 12/1986 Miller
4,633,878 A 1/1987 Bombardieri
4,637,403 A 1/1987 Garcia et al.
4,650,547 A 3/1987 Gough
4,654,197 A 3/1987 Lilja et al.
4,655,880 A 4/1987 Liu
4,655,885 A 4/1987 Hill et al.
4,671,288 A 6/1987 Gough
4,679,562 A 7/1987 Luksha
4,680,268 A 7/1987 Clark, Jr.
4,682,602 A 7/1987 Prohaska
4,684,537 A 8/1987 Graetzel et al.
4,685,463 A 8/1987 Williams
4,685,466 A 8/1987 Rau
4,703,756 A 11/1987 Gough et al.
4,711,245 A 12/1987 Higgins et al.
4,711,247 A 12/1987 Fishman
4,717,673 A 1/1988 Wrighton et al.
4,721,601 A 1/1988 Wrighton et al.
4,721,677 A 1/1988 Clark, Jr.
4,726,378 A 2/1988 Kaplan
4,726,716 A 2/1988 McGuire
4,729,672 A 3/1988 Takagi
4,731,726 A 3/1988 Allen, III
4,749,985 A 6/1988 Corsberg
4,755,173 A 7/1988 Konopka
4,757,022 A 7/1988 Shults et al.
4,758,323 A 7/1988 Davis et al.
4,759,371 A 7/1988 Franetzki
4,759,828 A 7/1988 Young et al.
4,764,416 A 8/1988 Ueyama et al.
4,776,944 A 10/1988 Janata et al.
4,777,953 A 10/1988 Ash et al.
4,779,618 A 10/1988 Mund et al.
4,781,683 A 11/1988 Wozniak et al.
4,781,798 A 11/1988 Gough
4,784,736 A 11/1988 Lonsdale et al.
4,795,707 A 1/1989 Niiyama et al.
4,796,634 A 1/1989 Huntsman et al.
4,805,624 A 2/1989 Yao et al.
4,813,424 A 3/1989 Wilkins
4,815,469 A 3/1989 Cohen et al.
4,820,399 A 4/1989 Senda et al.
4,822,337 A 4/1989 Newhouse et al.
4,830,959 A 5/1989 McNeil et al.

(56) References Cited

U.S. PATENT DOCUMENTS

| | | | |
|---|---|---|---|
| 4,832,797 | A | 5/1989 | Vadgama et al. |
| RE32,947 | E | 6/1989 | Dormer et al. |
| 4,840,893 | A | 6/1989 | Hill et al. |
| 4,848,351 | A | 7/1989 | Finch |
| 4,854,322 | A | 8/1989 | Ash et al. |
| 4,865,038 | A | 9/1989 | Rich et al. |
| 4,871,351 | A | 10/1989 | Feingold |
| 4,871,440 | A | 10/1989 | Nagata et al. |
| 4,874,500 | A | 10/1989 | Madou et al. |
| 4,890,620 | A | 1/1990 | Gough |
| 4,894,137 | A | 1/1990 | Takizawa et al. |
| 4,895,147 | A | 1/1990 | Bodicky et al. |
| 4,897,162 | A | 1/1990 | Lewandowski et al. |
| 4,897,173 | A | 1/1990 | Nankai et al. |
| 4,909,908 | A | 3/1990 | Ross et al. |
| 4,911,794 | A | 3/1990 | Parce et al. |
| 4,917,800 | A | 4/1990 | Lonsdale et al. |
| 4,919,141 | A | 4/1990 | Zier et al. |
| 4,919,767 | A | 4/1990 | Vadgama et al. |
| 4,923,586 | A | 5/1990 | Katayama et al. |
| 4,925,268 | A | 5/1990 | Iyer et al. |
| 4,927,516 | A | 5/1990 | Yamaguchi et al. |
| 4,934,369 | A | 6/1990 | Maxwell |
| 4,935,105 | A | 6/1990 | Churchouse |
| 4,935,345 | A | 6/1990 | Guibeau et al. |
| 4,938,860 | A | 7/1990 | Wogoman |
| 4,944,299 | A | 7/1990 | Silvian |
| 4,950,378 | A | 8/1990 | Nagara |
| 4,953,552 | A | 9/1990 | DeMarzo |
| 4,954,129 | A | 9/1990 | Giuliani et al. |
| 4,969,468 | A | 11/1990 | Byers et al. |
| 4,970,145 | A | 11/1990 | Bennetto et al. |
| 4,974,929 | A | 12/1990 | Curry |
| 4,986,271 | A | 1/1991 | Wilkins |
| 4,988,341 | A | 1/1991 | Columbus et al. |
| 4,994,167 | A | 2/1991 | Shults et al. |
| 4,995,402 | A | 2/1991 | Smith et al. |
| 5,000,180 | A | 3/1991 | Kuypers et al. |
| 5,001,054 | A | 3/1991 | Wagner |
| 5,002,054 | A | 3/1991 | Ash et al. |
| 5,013,161 | A | 5/1991 | Zaragoza et al. |
| 5,019,974 | A | 5/1991 | Beckers |
| 5,035,860 | A | 7/1991 | Kleingeld et al. |
| 5,036,860 | A | 8/1991 | Leigh et al. |
| 5,047,044 | A | 9/1991 | Smith et al. |
| 5,050,612 | A | 9/1991 | Matsumura |
| 5,055,171 | A | 10/1991 | Peck |
| 5,058,592 | A | 10/1991 | Whisler |
| 5,070,535 | A | 12/1991 | Hochmair et al. |
| 5,082,550 | A | 1/1992 | Rishpon et al. |
| 5,082,786 | A | 1/1992 | Nakamoto |
| 5,089,112 | A | 2/1992 | Skotheim et al. |
| 5,095,904 | A | 3/1992 | Seligman et al. |
| 5,101,814 | A | 4/1992 | Palti |
| 5,106,365 | A | 4/1992 | Hernandez |
| 5,108,564 | A | 4/1992 | Szuminsky et al. |
| 5,109,850 | A | 5/1992 | Blanco et al. |
| 5,120,420 | A | 6/1992 | Nankai et al. |
| 5,122,925 | A | 6/1992 | Inpyn |
| 5,126,034 | A | 6/1992 | Carter et al. |
| 5,133,856 | A | 7/1992 | Yamaguchi et al. |
| 5,135,003 | A | 8/1992 | Souma |
| 5,140,985 | A | 8/1992 | Schroeder et al. |
| 5,141,868 | A | 8/1992 | Shanks et al. |
| 5,161,532 | A | 11/1992 | Joseph |
| 5,165,407 | A | 11/1992 | Wilson et al. |
| 5,174,291 | A | 12/1992 | Schoonen et al. |
| 5,190,041 | A | 3/1993 | Palti |
| 5,192,416 | A | 3/1993 | Wang et al. |
| 5,198,367 | A | 3/1993 | Aizawa et al. |
| 5,202,261 | A | 4/1993 | Musho et al. |
| 5,205,920 | A | 4/1993 | Oyama et al. |
| 5,208,154 | A | 5/1993 | Weaver et al. |
| 5,209,229 | A | 5/1993 | Gilli |
| 5,217,595 | A | 6/1993 | Smith et al. |
| 5,229,282 | A | 7/1993 | Yoshioka et al. |
| 5,234,835 | A | 8/1993 | Nestor et al. |
| 5,238,729 | A | 8/1993 | Debe |
| 5,246,867 | A | 9/1993 | Lakowicz et al. |
| 5,250,439 | A | 10/1993 | Musho et al. |
| 5,262,035 | A | 11/1993 | Gregg et al. |
| 5,262,305 | A | 11/1993 | Heller et al. |
| 5,264,103 | A | 11/1993 | Yoshioka et al. |
| 5,264,104 | A | 11/1993 | Gregg et al. |
| 5,264,105 | A | 11/1993 | Gregg et al. |
| 5,264,106 | A | 11/1993 | McAleer et al. |
| 5,271,815 | A | 12/1993 | Wong |
| 5,279,294 | A | 1/1994 | Anderson et al. |
| 5,284,156 | A | 2/1994 | Schramm et al. |
| 5,285,792 | A | 2/1994 | Sjoquist et al. |
| 5,286,362 | A | 2/1994 | Hoenes et al. |
| 5,286,364 | A | 2/1994 | Yacynych et al. |
| 5,288,636 | A | 2/1994 | Pollmann et al. |
| 5,293,546 | A | 3/1994 | Tadros et al. |
| 5,293,877 | A | 3/1994 | O'Hara et al. |
| 5,299,571 | A | 4/1994 | Mastrototaro |
| 5,320,098 | A | 6/1994 | Davidson |
| 5,320,715 | A | 6/1994 | Berg |
| 5,320,725 | A | 6/1994 | Gregg et al. |
| 5,322,063 | A | 6/1994 | Allen et al. |
| 5,337,747 | A | 8/1994 | Neftel |
| 5,340,722 | A | 8/1994 | Wolfbeis et al. |
| 5,342,789 | A | 8/1994 | Chick et al. |
| 5,352,348 | A | 10/1994 | Young et al. |
| 5,356,786 | A | 10/1994 | Heller et al. |
| 5,360,404 | A | 11/1994 | Novacek et al. |
| 5,368,028 | A | 11/1994 | Palti |
| 5,372,133 | A | 12/1994 | Hogen Esch |
| 5,372,427 | A | 12/1994 | Padovani et al. |
| 5,376,251 | A | 12/1994 | Kaneko et al. |
| 5,378,628 | A | 1/1995 | Gratzel et al. |
| 5,379,238 | A | 1/1995 | Stark |
| 5,387,327 | A | 2/1995 | Khan |
| 5,390,670 | A | 2/1995 | Centa et al. |
| 5,390,671 | A | 2/1995 | Lord et al. |
| 5,391,250 | A | 2/1995 | Cheney, II et al. |
| 5,395,504 | A | 3/1995 | Saurer et al. |
| 5,400,782 | A | 3/1995 | Beaubiah |
| 5,408,999 | A | 4/1995 | Singh et al. |
| 5,411,647 | A | 5/1995 | Johnson et al. |
| 5,425,361 | A | 6/1995 | Fenzlein et al. |
| 5,431,160 | A | 7/1995 | Wilkins |
| 5,431,921 | A | 7/1995 | Thombre |
| 5,437,999 | A | 8/1995 | Diebold et al. |
| 5,462,645 | A | 10/1995 | Albery et al. |
| 5,469,846 | A | 11/1995 | Khan |
| 5,489,414 | A | 2/1996 | Schreiber et al. |
| 5,491,474 | A | 2/1996 | Suni et al. |
| 5,494,562 | A | 2/1996 | Maley et al. |
| 5,496,453 | A | 3/1996 | Uenoyama et al. |
| 5,497,772 | A | 3/1996 | Schulman et al. |
| 5,507,288 | A | 4/1996 | Bocker et al. |
| 5,509,410 | A | 4/1996 | Hill et al. |
| 5,514,718 | A | 5/1996 | Lewis et al. |
| 5,531,878 | A | 7/1996 | Vadgama et al. |
| 5,543,326 | A | 8/1996 | Heller et al. |
| 5,545,191 | A | 8/1996 | Mann et al. |
| 5,551,427 | A | 9/1996 | Altman |
| 5,560,357 | A | 10/1996 | Faupei et al. |
| 5,562,713 | A | 10/1996 | Silvian |
| 5,565,085 | A | 10/1996 | Ikeda et al. |
| 5,567,302 | A | 10/1996 | Song et al. |
| 5,568,806 | A | 10/1996 | Cheney, II et al. |
| 5,569,186 | A | 10/1996 | Lord et al. |
| 5,575,563 | A | 11/1996 | Chiu et al. |
| 5,582,184 | A | 12/1996 | Erickson et al. |
| 5,582,697 | A | 12/1996 | Ikeda et al. |
| 5,582,698 | A | 12/1996 | Flaherty et al. |
| 5,584,813 | A | 12/1996 | Livingston et al. |
| 5,586,553 | A | 12/1996 | Halili et al. |
| 5,589,326 | A | 12/1996 | Deng et al. |
| 5,593,852 | A | 1/1997 | Heller et al. |
| 5,596,150 | A | 1/1997 | Arndt et al. |
| 5,601,435 | A | 2/1997 | Quy |

(56) References Cited

U.S. PATENT DOCUMENTS 5,613,978 A 3/1997 Harding
5,617,851 A 4/1997 Lipkovker
5,628,310 A 5/1997 Rao et al.
5,628,890 A 5/1997 Carter et al.
5,632,557 A 5/1997 Simons
5,651,869 A 7/1997 Yoshioka et al.
5,653,239 A 8/1997 Pompei et al.
5,660,163 A 8/1997 Schulman et al.
5,665,071 A 9/1997 Wyrick
5,665,222 A 9/1997 Heller et al.
5,670,031 A 9/1997 Hintsche et al.
5,680,858 A 10/1997 Hansen et al.
5,682,233 A 10/1997 Brinda
5,693,024 A * 12/1997 Flower .................... A61N 1/30 604/20
5,695,623 A 12/1997 Michel et al.
5,708,247 A 1/1998 McAleer et al.
5,711,001 A 1/1998 Bussan et al.
5,711,297 A 1/1998 Iliff et al.
5,711,861 A 1/1998 Ward et al.
5,711,862 A 1/1998 Sakoda et al.
5,733,044 A 3/1998 Rose et al.
5,735,285 A 4/1998 Albert et al.
5,741,211 A 4/1998 Renirie et al.
5,743,262 A 4/1998 Lepper, Jr. et al.
5,746,697 A 5/1998 Swedlow et al.
5,749,656 A 5/1998 Boehm et al.
5,766,131 A 6/1998 Kondo et al.
5,771,001 A 6/1998 Cobb
5,772,586 A 6/1998 Heinonen et al.
5,779,665 A 7/1998 Mastrototaro et al.
5,791,344 A 8/1998 Schulman et al.
5,800,420 A 9/1998 Gross et al.
5,807,375 A 9/1998 Gross et al.
5,814,020 A 9/1998 Gross
5,820,551 A 10/1998 Hill et al.
5,820,622 A 10/1998 Gross et al.
5,822,715 A 10/1998 Worthington et al.
5,827,184 A 10/1998 Netherly et al.
5,840,020 A 11/1998 Heinonen et al.
5,842,983 A 12/1998 Abel et al.
5,851,197 A 12/1998 Marano et al.
5,858,001 A 1/1999 Tsals et al.
5,885,211 A 3/1999 Eppstein et al.
5,899,855 A 5/1999 Brown
5,918,603 A 7/1999 Brown
5,924,979 A 7/1999 Sedlow et al.
5,925,021 A 7/1999 Castellano et al.
5,931,814 A 8/1999 Gross et al.
5,931,868 A 8/1999 Gross et al.
5,938,679 A 8/1999 Freeman
5,942,979 A 8/1999 Luppino
5,948,006 A 9/1999 Mann
5,951,521 A 9/1999 Mastrototaro et al.
5,951,582 A 9/1999 Thome et al.
5,954,643 A 9/1999 Antwerp
5,954,685 A 9/1999 Tierny
5,957,854 A 9/1999 Besson et al.
5,961,451 A 10/1999 Reber et al.
5,964,993 A 10/1999 Blubaugh, Jr. et al.
5,965,380 A 10/1999 Heller et al.
5,971,922 A 10/1999 Arita et al.
5,972,199 A 10/1999 Heller et al.
5,987,353 A 11/1999 Khatchatrian et al.
5,993,411 A 11/1999 Choi
5,995,860 A 11/1999 Sun et al.
5,997,501 A 12/1999 Gross et al.
6,001,067 A 12/1999 Shults et al.
6,004,278 A 12/1999 Botich et al.
6,017,335 A 1/2000 Burnham
6,022,368 A 2/2000 Gavronsky et al.
6,024,699 A 2/2000 Surwit et al.
6,026,321 A 2/2000 Miyata et al.
6,027,459 A 2/2000 Shain et al.
6,049,727 A 4/2000 Crothall
6,056,718 A 5/2000 Funderburk et al.
6,059,946 A 5/2000 Yukawa et al.
6,068,399 A 5/2000 Tseng
6,071,391 A 6/2000 Gotoh et al.
6,083,710 A 7/2000 Heller et al.
6,088,608 A 7/2000 Schulman et al.
6,091,975 A 7/2000 Daddona et al.
6,091,976 A 7/2000 Pfeiffer et al.
6,093,172 A 7/2000 Funderburk et al.
6,096,066 A * 8/2000 Chen ...................... A61N 5/062 607/91
6,103,033 A 8/2000 Say et al.
6,117,290 A 9/2000 Say et al.
6,119,028 A 9/2000 Schulman et al.
6,120,676 A 9/2000 Heller et al.
6,121,009 A 9/2000 Heller et al.
6,121,611 A 9/2000 Lindsay et al.
6,122,351 A 9/2000 Schlueter, Jr. et al.
6,134,461 A 10/2000 Say et al.
6,143,164 A 11/2000 Heller et al.
6,144,837 A 11/2000 Quy
6,159,147 A 12/2000 Lichter et al.
6,161,095 A 12/2000 Brown
6,162,611 A 12/2000 Heller et al.
6,175,752 B1 1/2001 Say et al.
6,186,982 B1 2/2001 Gross et al.
6,200,265 B1 3/2001 Walsh et al.
6,212,416 B1 4/2001 Ward et al.
6,219,574 B1 4/2001 Cormier et al.
6,248,067 B1 6/2001 Causey, III et al.
6,254,536 B1 7/2001 DeVito
6,254,586 B1 7/2001 Mann et al.
6,270,455 B1 8/2001 Brown
6,275,717 B1 8/2001 Gross et al.
6,283,761 B1 9/2001 Joao
6,283,982 B1 9/2001 Levaughn et al.
6,284,478 B1 9/2001 Heller et al.
6,293,925 B1 9/2001 Safabash et al.
6,295,506 B1 9/2001 Heinonen et al.
6,299,757 B1 10/2001 Feldman et al.
6,302,866 B1 10/2001 Marggi
6,306,104 B1 10/2001 Cunningham et al.
6,309,884 B1 10/2001 Cooper et al.
6,329,161 B1 12/2001 Heller et al.
6,331,244 B1 12/2001 Lewis et al.
6,338,790 B1 1/2002 Feldman et al.
6,348,640 B1 2/2002 Navot et al.
6,359,444 B1 3/2002 Grimes
6,360,888 B1 3/2002 McIvor et al.
6,366,794 B1 4/2002 Moussy et al.
6,368,141 B1 4/2002 Antwerp et al.
6,368,274 B1 4/2002 Van Antwerp et al.
6,377,828 B1 4/2002 Chaiken et al.
6,377,894 B1 4/2002 Deweese et al.
6,379,301 B1 4/2002 Worthington et al.
6,409,740 B1 6/2002 Kuhr et al.
6,413,393 B1 7/2002 Van Antwerp et al.
6,418,332 B1 7/2002 Mastrototaro et al.
6,424,847 B1 7/2002 Mastrototaro et al.
6,427,088 B1 7/2002 Bowman, IV et al.
6,433,743 B1 8/2002 Massy et al.
6,435,017 B1 8/2002 Nowicki, Jr. et al.
6,437,679 B1 8/2002 Roques
6,440,068 B1 8/2002 Brown et al.
6,445,374 B2 9/2002 Albert et al.
6,461,496 B1 10/2002 Feldman et al.
6,478,736 B1 11/2002 Mault
6,482,176 B1 11/2002 Wich
6,484,045 B1 11/2002 Holker et al.
6,484,046 B1 11/2002 Say et al.
6,503,381 B1 1/2003 Gotoh et al.
6,514,460 B1 2/2003 Fendrock
6,514,718 B2 2/2003 Heller et al.
6,520,326 B2 2/2003 Mclvor et al.
6,540,891 B1 4/2003 Stewart et al.
6,546,268 B1 4/2003 Ishikawa et al.
6,551,494 B1 4/2003 Heller et al.
6,551,496 B1 4/2003 Moles et al.
6,554,795 B2 4/2003 Lam et al.

(56) References Cited

U.S. PATENT DOCUMENTS 6,558,320 B1 5/2003 Causey, III et al.
6,558,321 B1 5/2003 Burd et al.
6,560,471 B1 5/2003 Heller et al.
6,561,978 B1 5/2003 Conn et al.
6,562,001 B2 5/2003 Lebel et al.
6,564,105 B2 5/2003 Starkweather et al.
6,565,509 B1 5/2003 Say et al.
6,571,128 B2 5/2003 Lebel et al.
6,572,566 B2 6/2003 Effenhauser
6,576,101 B1 6/2003 Heller et al.
6,577,899 B2 6/2003 Lebel et al.
6,579,690 B1 6/2003 Bonnecaze et al.
6,585,644 B2 7/2003 Lebel et al.
6,589,229 B1 7/2003 Connelly et al.
6,591,125 B1 7/2003 Buse et al.
6,592,745 B1 7/2003 Feldman et al.
6,595,919 B2 7/2003 Berner et al.
6,600,997 B2 7/2003 Deweese et al.
6,605,200 B1 8/2003 Mao et al.
6,605,201 B1 8/2003 Mao et al.
6,607,509 B2 8/2003 Bobroff et al.
6,610,012 B2 8/2003 Mault
6,616,819 B1 9/2003 Liamos et al.
6,618,934 B1 9/2003 Feldman et al.
6,633,772 B2 10/2003 Ford et al.
6,635,014 B2 10/2003 Starkweather et al.
6,648,821 B2 11/2003 Lebel et al.
6,650,471 B2 11/2003 Doi
6,654,625 B1 11/2003 Say et al.
6,659,948 B2 12/2003 Lebel et al.
6,666,849 B1 12/2003 Marshall et al.
6,668,196 B1 12/2003 Villegas et al.
6,676,290 B1 1/2004 Lu
6,687,546 B2 2/2004 Lebel et al.
6,689,056 B1 2/2004 Kilcoyne et al.
6,694,191 B2 2/2004 Starkweather et al.
6,695,860 B1 2/2004 Ward et al.
6,699,218 B2 3/2004 Flaherty et al.
6,702,857 B2 3/2004 Brauker et al.
6,730,200 B1 5/2004 Stewart et al.
6,733,446 B2 5/2004 Lebel et al.
6,736,957 B1 5/2004 Forrow et al.
6,740,075 B2 5/2004 Lebel et al.
6,741,877 B1 5/2004 Shults et al.
6,746,582 B2 6/2004 Heller et al.
6,749,740 B2 6/2004 Liamos et al.
6,758,810 B2 7/2004 Lebel et al.
6,764,581 B1 7/2004 Forrow et al.
6,770,030 B1 8/2004 Schaupp et al.
6,773,671 B1 8/2004 Lewis et al.
6,790,178 B1 9/2004 Mault et al.
6,809,653 B1 10/2004 Mann et al.
6,810,290 B2 10/2004 Lebel et al.
6,811,533 B2 11/2004 Lebel et al.
6,811,534 B2 11/2004 Bowman, IV et al.
6,813,519 B2 11/2004 Lebel et al.
6,830,551 B1 12/2004 Uchigaki et al.
6,837,858 B2 1/2005 Cunningham et al.
6,837,885 B2 1/2005 Koblish et al.
6,837,988 B2 1/2005 Leong et al.
6,849,052 B2 2/2005 Ughigaki et al.
6,854,882 B2 2/2005 Chen
6,862,465 B2 3/2005 Shults et al.
6,873,268 B2 3/2005 Lebel et al.
6,881,551 B2 4/2005 Heller et al.
6,892,085 B2 5/2005 McIvor et al.
6,893,545 B2 5/2005 Gotoh et al.
6,895,265 B2 5/2005 Silver
6,923,763 B1 8/2005 Kovatchev et al.
6,931,327 B2 8/2005 Goode, Jr. et al.
6,932,892 B2 8/2005 Chen
6,932,894 B2 8/2005 Mao et al.
6,936,006 B2 8/2005 Sabra
6,942,518 B2 9/2005 Liamos et al.
6,950,708 B2 9/2005 Bowman IV et al.
6,958,705 B2 10/2005 Lebel et al.
6,960,192 B1 * 11/2005 Flaherty ............ A61M 5/14248 604/185
6,968,294 B2 11/2005 Gutta et al.
6,971,274 B2 12/2005 Olin
6,971,999 B2 12/2005 Py et al.
6,974,437 B2 12/2005 Lebel et al.
6,990,366 B2 1/2006 Say et al.
6,997,907 B2 2/2006 Safabash et al.
6,998,247 B2 2/2006 Monfre et al.
7,003,336 B2 2/2006 Holker et al.
7,003,340 B2 2/2006 Say et al.
7,003,341 B2 2/2006 Say et al.
7,024,245 B2 4/2006 Lebel et al.
7,025,743 B2 4/2006 Mann et al.
7,041,068 B2 5/2006 Freeman et al.
7,041,468 B2 5/2006 Drucker et al.
7,052,483 B2 5/2006 Wojcik
7,056,302 B2 6/2006 Douglas
7,074,307 B2 7/2006 Simpson et al.
7,081,195 B2 7/2006 Simpson et al.
7,098,803 B2 8/2006 Mann et al.
7,108,778 B2 9/2006 Simpson et al.
7,110,803 B2 9/2006 Shults et al.
7,113,821 B1 9/2006 Sun et al.
7,134,999 B2 11/2006 Brauker et al.
7,136,689 B2 11/2006 Shults et al.
7,167,818 B2 1/2007 Brown
7,171,274 B2 1/2007 Starkweather et al.
7,190,988 B2 3/2007 Say et al.
7,192,450 B2 3/2007 Brauker et al.
7,198,606 B2 4/2007 Boecker et al.
7,207,974 B2 4/2007 Safabash et al.
7,226,978 B2 6/2007 Tapsak et al.
7,276,029 B2 10/2007 Goode, Jr. et al.
7,278,983 B2 10/2007 Ireland et al.
7,297,151 B2 11/2007 Boecker et al.
7,299,082 B2 11/2007 Feldman et al.
7,310,544 B2 12/2007 Brister et al.
7,318,816 B2 1/2008 Bobroff et al.
7,324,012 B2 1/2008 Mann et al.
7,329,239 B2 2/2008 Safabash et al.
7,335,294 B2 2/2008 Heller et al.
7,340,287 B2 3/2008 Mason et al.
7,340,309 B2 3/2008 Miazga et al.
7,354,420 B2 4/2008 Steil et al.
7,364,592 B2 4/2008 Carr-Brendel et al.
7,366,556 B2 4/2008 Brister et al.
7,379,765 B2 5/2008 Petisce et al.
7,381,184 B2 6/2008 Funderburk et al.
7,402,153 B2 7/2008 Steil et al.
7,416,541 B2 8/2008 Yuzhakov et al.
7,424,318 B2 9/2008 Brister et al.
7,455,663 B2 11/2008 Bikovsky
7,460,898 B2 12/2008 Brister et al.
7,462,264 B2 12/2008 Heller et al.
7,467,003 B2 12/2008 Brister et al.
7,471,972 B2 12/2008 Rhodes et al.
7,494,465 B2 2/2009 Brister et al.
7,497,827 B2 3/2009 Brister et al.
7,499,002 B2 3/2009 Blasko et al.
7,519,408 B2 4/2009 Rasdal et al.
7,583,990 B2 9/2009 Goode, Jr. et al.
7,591,801 B2 9/2009 Brauker et al.
7,599,726 B2 10/2009 Goode, Jr. et al.
7,604,592 B2 10/2009 Freeman et al.
7,613,491 B2 11/2009 Boock et al.
7,615,007 B2 11/2009 Shults et al.
7,632,228 B2 12/2009 Brauker et al.
7,637,868 B2 12/2009 Saint et al.
7,640,048 B2 12/2009 Dobbles et al.
7,651,596 B2 1/2010 Petisce et al.
7,654,956 B2 2/2010 Brister et al.
7,657,297 B2 2/2010 Simpson et al.
7,666,149 B2 2/2010 Simons et al.
7,682,338 B2 3/2010 Griffin
7,697,967 B2 4/2010 Stafford
7,711,402 B2 5/2010 Shults et al.
7,713,574 B2 5/2010 Brister et al.

(56) References Cited

U.S. PATENT DOCUMENTS

| | | | | |
|---|---|---|---|---|
| 7,715,893 | B2 | 5/2010 | Kamath et al. | |
| 7,736,344 | B2 | 6/2010 | Moberg et al. | |
| 7,763,042 | B2 | 7/2010 | Iio et al. | |
| 7,766,829 | B2 | 8/2010 | Sloan et al. | |
| 7,866,026 | B1 | 1/2011 | Wang et al. | |
| 7,955,297 | B2 | 6/2011 | Radmer et al. | |
| 8,062,253 | B2 | 11/2011 | Nielsen et al. | |
| 8,298,172 | B2 | 10/2012 | Nielsen | |
| 9,072,476 | B2 * | 7/2015 | Shah | A61B 5/6849 |
| 9,259,175 | B2 * | 2/2016 | Stafford | A61M 5/14248 |
| 10,363,363 | B2 * | 7/2019 | Stafford | A61M 5/14248 |
| 2002/0013538 | A1 | 1/2002 | Teller | |
| 2002/0019022 | A1 | 2/2002 | Dunn et al. | |
| 2002/0022855 | A1 | 2/2002 | Bobroff et al. | |
| 2002/0040208 | A1 * | 4/2002 | Flaherty | A61M 5/14248 604/67 |
| 2002/0042090 | A1 | 4/2002 | Heller et al. | |
| 2002/0050250 | A1 | 5/2002 | Peterson et al. | |
| 2002/0055711 | A1 | 5/2002 | Lavi et al. | |
| 2002/0057993 | A1 | 5/2002 | Maisey et al. | |
| 2002/0066764 | A1 | 6/2002 | Perry et al. | |
| 2002/0076966 | A1 | 6/2002 | Carron et al. | |
| 2002/0082487 | A1 | 6/2002 | Kollias et al. | |
| 2002/0103499 | A1 | 8/2002 | Perez et al. | |
| 2002/0106709 | A1 | 8/2002 | Potts et al. | |
| 2002/0119711 | A1 | 8/2002 | VanAntwerp et al. | |
| 2002/0128594 | A1 | 9/2002 | Das et al. | |
| 2002/0130042 | A1 | 9/2002 | Moerman et al. | |
| 2002/0133066 | A1 | 9/2002 | Miller et al. | |
| 2002/0154050 | A1 | 10/2002 | Krupp et al. | |
| 2002/0161288 | A1 | 10/2002 | Shin et al. | |
| 2002/0161290 | A1 | 10/2002 | Chance | |
| 2002/0165462 | A1 | 11/2002 | Westbrook et al. | |
| 2002/0169369 | A1 | 11/2002 | Ward et al. | |
| 2002/0198444 | A1 | 12/2002 | Ughigaki et al. | |
| 2003/0002682 | A1 | 1/2003 | Smith et al. | |
| 2003/0023317 | A1 | 1/2003 | Brauker et al. | |
| 2003/0023461 | A1 | 1/2003 | Quintanilla et al. | |
| 2003/0028089 | A1 | 2/2003 | Galley et al. | |
| 2003/0032867 | A1 | 2/2003 | Crothall et al. | |
| 2003/0032874 | A1 | 2/2003 | Rhodes et al. | |
| 2003/0042137 | A1 | 3/2003 | Mao et al. | |
| 2003/0065308 | A1 | 4/2003 | Lebel et al. | |
| 2003/0069510 | A1 | 4/2003 | Semler | |
| 2003/0078560 | A1 | 4/2003 | Miller et al. | |
| 2003/0083686 | A1 | 5/2003 | Freeman et al. | |
| 2003/0097092 | A1 | 5/2003 | Flaherty | |
| 2003/0100040 | A1 | 5/2003 | Bonnecaze et al. | |
| 2003/0109775 | A1 | 6/2003 | O'Neil et al. | |
| 2003/0134347 | A1 | 7/2003 | Heller et al. | |
| 2003/0135333 | A1 | 7/2003 | Aceti et al. | |
| 2003/0144581 | A1 | 7/2003 | Conn et al. | |
| 2003/0144608 | A1 | 7/2003 | Kojima et al. | |
| 2003/0155656 | A1 | 8/2003 | Chiu et al. | |
| 2003/0168338 | A1 | 9/2003 | Gao et al. | |
| 2003/0176933 | A1 | 9/2003 | Lebel et al. | |
| 2003/0187338 | A1 | 10/2003 | Say et al. | |
| 2003/0198558 | A1 * | 10/2003 | Nason | F04B 17/00 417/328 |
| 2003/0199790 | A1 | 10/2003 | Boecker et al. | |
| 2003/0199910 | A1 | 10/2003 | Boecker et al. | |
| 2003/0212379 | A1 | 11/2003 | Bylund et al. | |
| 2003/0217966 | A1 | 11/2003 | Tapsak et al. | |
| 2003/0225361 | A1 | 12/2003 | Sabra | |
| 2004/0010207 | A1 | 1/2004 | Flaherty et al. | |
| 2004/0011671 | A1 | 1/2004 | Shults et al. | |
| 2004/0040840 | A1 | 3/2004 | Mao et al. | |
| 2004/0045879 | A1 | 3/2004 | Shults et al. | |
| 2004/0054263 | A1 | 3/2004 | Moerman et al. | |
| 2004/0064068 | A1 | 4/2004 | DeNuzzio et al. | |
| 2004/0064133 | A1 | 4/2004 | Miller et al. | |
| 2004/0072357 | A1 | 4/2004 | Steine et al. | |
| 2004/0096959 | A1 | 5/2004 | Steine et al. | |
| 2004/0106858 | A1 | 6/2004 | Say et al. | |
| 2004/0106859 | A1 | 6/2004 | Say et al. | |
| 2004/0116847 | A1 | 6/2004 | Wall | |
| 2004/0116865 | A1 | 6/2004 | Bengtsson | |
| 2004/0122353 | A1 | 6/2004 | Shahmirian et al. | |
| 2004/0122489 | A1 | 6/2004 | Mazar et al. | |
| 2004/0133164 | A1 | 7/2004 | Funderburk et al. | |
| 2004/0135684 | A1 | 7/2004 | Steinthal et al. | |
| 2004/0138544 | A1 | 7/2004 | Ward et al. | |
| 2004/0138588 | A1 | 7/2004 | Saikley et al. | |
| 2004/0138688 | A1 | 7/2004 | Giraud | |
| 2004/0140211 | A1 | 7/2004 | Broy et al. | |
| 2004/0147996 | A1 | 7/2004 | Miazga et al. | |
| 2004/0158207 | A1 | 8/2004 | Hunn et al. | |
| 2004/0167801 | A1 | 8/2004 | Say et al. | |
| 2004/0171910 | A1 | 9/2004 | Moore-Steele | |
| 2004/0171921 | A1 | 9/2004 | Say et al. | |
| 2004/0176672 | A1 | 9/2004 | Silver et al. | |
| 2004/0186362 | A1 | 9/2004 | Brauker et al. | |
| 2004/0186365 | A1 | 9/2004 | Jin et al. | |
| 2004/0193090 | A1 | 9/2004 | Lebel et al. | |
| 2004/0199059 | A1 | 10/2004 | Brauker et al. | |
| 2004/0204687 | A1 | 10/2004 | Mogensen et al. | |
| 2004/0210122 | A1 | 10/2004 | Sleburg | |
| 2004/0223985 | A1 | 11/2004 | Dunfiled et al. | |
| 2004/0225338 | A1 | 11/2004 | Lebel et al. | |
| 2004/0236200 | A1 | 11/2004 | Say et al. | |
| 2004/0236251 | A1 | 11/2004 | Roe et al. | |
| 2004/0254433 | A1 | 12/2004 | Bandis et al. | |
| 2004/0254434 | A1 | 12/2004 | Goodnow et al. | |
| 2004/0267300 | A1 | 12/2004 | Mace | |
| 2005/0003470 | A1 | 1/2005 | Nelson et al. | |
| 2005/0004494 | A1 | 1/2005 | Perez et al. | |
| 2005/0006122 | A1 | 1/2005 | Burnette | |
| 2005/0010269 | A1 | 1/2005 | Lebel et al. | |
| 2005/0027177 | A1 | 2/2005 | Shin et al. | |
| 2005/0027180 | A1 | 2/2005 | Goode et al. | |
| 2005/0031689 | A1 | 2/2005 | Shults et al. | |
| 2005/0038331 | A1 * | 2/2005 | Silaski | A61B 5/14865 600/347 |
| 2005/0043598 | A1 | 2/2005 | Goode et al. | |
| 2005/0070819 | A1 | 3/2005 | Poux et al. | |
| 2005/0085872 | A1 | 4/2005 | Yanagihara et al. | |
| 2005/0090607 | A1 | 4/2005 | Tapsak et al. | |
| 2005/0090850 | A1 | 4/2005 | Thoes et al. | |
| 2005/0096520 | A1 | 5/2005 | Maekawa et al. | |
| 2005/0106713 | A1 | 5/2005 | Phan et al. | |
| 2005/0112169 | A1 | 5/2005 | Brauker et al. | |
| 2005/0114068 | A1 | 5/2005 | Chey et al. | |
| 2005/0121322 | A1 | 6/2005 | Say et al. | |
| 2005/0131346 | A1 | 6/2005 | Douglas | |
| 2005/0143635 | A1 | 6/2005 | Kamath et al. | |
| 2005/0154410 | A1 | 7/2005 | Conway et al. | |
| 2005/0165404 | A1 | 7/2005 | Miller | |
| 2005/0173245 | A1 | 8/2005 | Feldman et al. | |
| 2005/0176136 | A1 | 8/2005 | Burd et al. | |
| 2005/0182306 | A1 | 8/2005 | Sloan | |
| 2005/0187720 | A1 | 8/2005 | Goode et al. | |
| 2005/0192557 | A1 | 9/2005 | Brauker et al. | |
| 2005/0195930 | A1 | 9/2005 | Spital et al. | |
| 2005/0197554 | A1 | 9/2005 | Polcha | |
| 2005/0203360 | A1 | 9/2005 | Brauker et al. | |
| 2005/0222518 | A1 | 10/2005 | Dib | |
| 2005/0222599 | A1 | 10/2005 | Czernecki et al. | |
| 2005/0236277 | A9 | 10/2005 | Imran et al. | |
| 2005/0239154 | A1 | 10/2005 | Feldman et al. | |
| 2005/0239156 | A1 | 10/2005 | Drucker et al. | |
| 2005/0241957 | A1 | 11/2005 | Mao et al. | |
| 2005/0245795 | A1 | 11/2005 | Goode et al. | |
| 2005/0245799 | A1 | 11/2005 | Brauker et al. | |
| 2005/0245844 | A1 | 11/2005 | Mace et al. | |
| 2005/0267327 | A1 | 12/2005 | Iizuka et al. | |
| 2005/0277164 | A1 | 12/2005 | Drucker et al. | |
| 2005/0283114 | A1 | 12/2005 | Bresina et al. | |
| 2005/0287620 | A1 | 12/2005 | Heller et al. | |
| 2006/0001538 | A1 | 1/2006 | Kraft et al. | |
| 2006/0004303 | A1 | 1/2006 | Weidenhaupt et al. | |
| 2006/0009727 | A1 | 1/2006 | O'Mahony et al. | |
| 2006/0010098 | A1 | 1/2006 | Goodnow et al. | |
| 2006/0015020 | A1 | 1/2006 | Neale et al. | |
| 2006/0015024 | A1 | 1/2006 | Brister et al. | |

(56) References Cited

U.S. PATENT DOCUMENTS

2006/0016700 A1 1/2006 Brister et al.
2006/0019327 A1 1/2006 Brister et al.
2006/0020186 A1 1/2006 Brister et al.
2006/0020187 A1 1/2006 Brister et al.
2006/0020188 A1 1/2006 Kamath et al.
2006/0020189 A1 1/2006 Brister et al.
2006/0020190 A1 1/2006 Kamath et al.
2006/0020191 A1 1/2006 Brister et al.
2006/0020192 A1 1/2006 Brister et al.
2006/0020300 A1 1/2006 Nghiem et al.
2006/0025662 A1 2/2006 Buse et al.
2006/0036139 A1 2/2006 Brister et al.
2006/0036140 A1 2/2006 Brister et al.
2006/0036141 A1 2/2006 Kamath et al.
2006/0036142 A1 2/2006 Brister et al.
2006/0036143 A1 2/2006 Brister et al.
2006/0036144 A1 2/2006 Brister et al.
2006/0036145 A1 2/2006 Brister et al.
2006/0047220 A1 3/2006 Sakata et al.
2006/0091006 A1 5/2006 Wang et al.
2006/0129173 A1 6/2006 Wilkinson
2006/0155210 A1 7/2006 Beckman et al.
2006/0155317 A1 7/2006 List
2006/0173444 A1 8/2006 Choy et al.
2006/0189939 A1 8/2006 Gonnelli et al.
2006/0193375 A1 8/2006 Lee
2006/0200181 A1 9/2006 Fukuzawa et al.
2006/0222566 A1 10/2006 Brauker et al.
2006/0247508 A1 11/2006 Fennell
2006/0253086 A1* 11/2006 Moberg ................ A61M 5/158 604/272
2006/0258929 A1 11/2006 Goode et al.
2006/0264888 A1* 11/2006 Moberg .............. A61M 5/1723 604/93.01
2006/0276724 A1 12/2006 Freeman et al.
2006/0282042 A1 12/2006 Walters et al.
2006/0287591 A1 12/2006 Ocvirk et al.
2007/0016381 A1 1/2007 Kamath et al.
2007/0027381 A1 2/2007 Stafford
2007/0038044 A1 2/2007 Dobbles et al.
2007/0056858 A1 3/2007 Chen et al.
2007/0060814 A1 3/2007 Stafford
2007/0068807 A1 3/2007 Feldman et al.
2007/0073129 A1 3/2007 Shah et al.
2007/0078320 A1 4/2007 Stafford
2007/0078321 A1 4/2007 Mazza et al.
2007/0078322 A1 4/2007 Stafford
2007/0088377 A1 4/2007 Levaughn et al.
2007/0095661 A1 5/2007 Wang et al.
2007/0106135 A1 5/2007 Sloan et al.
2007/0108048 A1 5/2007 Wang et al.
2007/0110124 A1 5/2007 Zaragoza et al.
2007/0149875 A1 6/2007 Ouyang et al.
2007/0163880 A1 7/2007 Woo et al.
2007/0173706 A1 7/2007 Neinast et al.
2007/0173741 A1 7/2007 Deshmukh et al.
2007/0191701 A1 8/2007 Feldman et al.
2007/0199818 A1 8/2007 Petyt et al.
2007/0203407 A1 8/2007 Hoss et al.
2007/0203966 A1 8/2007 Brauker et al.
2007/0213611 A1 9/2007 Simpson et al.
2007/0219496 A1 9/2007 Kamen et al.
2007/0227911 A1 10/2007 Wang et al.
2007/0232879 A1 10/2007 Brister et al.
2007/0233013 A1 10/2007 Schoenberg et al.
2007/0235331 A1 10/2007 Simpson et al.
2007/0244368 A1 10/2007 Bayloff et al.
2007/0244379 A1 10/2007 Boock et al.
2007/0244398 A1 10/2007 Lo et al.
2007/0249922 A1 10/2007 Peyser et al.
2007/0255302 A1 11/2007 Koeppel et al.
2008/0004512 A1 1/2008 Funderbunk et al.
2008/0009692 A1 1/2008 Stafford
2008/0009805 A1 1/2008 Ethelfeld
2008/0017522 A1 1/2008 Heller et al.
2008/0021666 A1 1/2008 Goode, Jr. et al.
2008/0027474 A1 1/2008 Curry et al.
2008/0029391 A1 2/2008 Mao et al.
2008/0033254 A1 2/2008 Kamath et al.
2008/0033268 A1 2/2008 Stafford
2008/0033318 A1 2/2008 Mace et al.
2008/0039702 A1 2/2008 Hayter et al.
2008/0045824 A1 2/2008 Tapsak et al.
2008/0064937 A1 3/2008 McGarraugh et al.
2008/0064941 A1 3/2008 Funderbunk et al.
2008/0065646 A1 3/2008 Zhang et al.
2008/0066305 A1 3/2008 Wang et al.
2008/0071156 A1 3/2008 Brister et al.
2008/0083617 A1 4/2008 Simpson et al.
2008/0086042 A1 4/2008 Brister et al.
2008/0086273 A1 4/2008 Shults et al.
2008/0097246 A1 4/2008 Stafford
2008/0099332 A1 5/2008 Scott et al.
2008/0112848 A1 5/2008 Huffstodt et al.
2008/0119707 A1* 5/2008 Stafford ............. A61B 5/14503 604/27
2008/0129486 A1 6/2008 Jeckelmann et al.
2008/0133702 A1 6/2008 Sharma et al.
2008/0147041 A1 6/2008 Kristensen
2008/0161664 A1 7/2008 Mastrototaro et al.
2008/0167578 A1 7/2008 Bryer et al.
2008/0183061 A1 7/2008 Goode et al.
2008/0188731 A1 8/2008 Brister et al.
2008/0189051 A1 8/2008 Goode et al.
2008/0194935 A1 8/2008 Brister et al.
2008/0194936 A1 8/2008 Goode et al.
2008/0194937 A1 8/2008 Goode et al.
2008/0194938 A1 8/2008 Brister et al.
2008/0195049 A1 8/2008 Thalmann et al.
2008/0195232 A1 8/2008 Carr-Brendel et al.
2008/0195967 A1 8/2008 Goode et al.
2008/0197024 A1 8/2008 Simpson et al.
2008/0200788 A1 8/2008 Brister et al.
2008/0200789 A1 8/2008 Brister et al.
2008/0200791 A1 8/2008 Simpson et al.
2008/0200897 A1 8/2008 Hoss et al.
2008/0208025 A1 8/2008 Shults et al.
2008/0214481 A1 9/2008 Challoner et al.
2008/0214915 A1 9/2008 Brister et al.
2008/0214918 A1 9/2008 Brister et al.
2008/0228051 A1 9/2008 Shults et al.
2008/0228054 A1 9/2008 Shults et al.
2008/0242961 A1 10/2008 Brister et al.
2008/0262330 A1 10/2008 Reynolds et al.
2008/0262469 A1 10/2008 Brister et al.
2008/0269673 A1 10/2008 Butoi et al.
2008/0275313 A1 11/2008 Brister et al.
2008/0283396 A1 11/2008 Wang et al.
2008/0287764 A1 11/2008 Rasdal et al.
2008/0287765 A1 11/2008 Rasdal et al.
2008/0287766 A1 11/2008 Rasdal et al.
2008/0294096 A1 11/2008 Uber et al.
2008/0296155 A1 12/2008 Shults et al.
2008/0300476 A1 12/2008 Stafford
2008/0306368 A1 12/2008 Goode, Jr. et al.
2008/0306434 A1 12/2008 Dobbles et al.
2008/0306435 A1 12/2008 Kamath et al.
2008/0306444 A1 12/2008 Brister et al.
2009/0005659 A1 1/2009 Kollias et al.
2009/0012377 A1 1/2009 Jennewine et al.
2009/0012379 A1 1/2009 Goode, Jr. et al.
2009/0018424 A1 1/2009 Kamath et al.
2009/0030294 A1 1/2009 Petisce et al.
2009/0036758 A1 2/2009 Brauker et al.
2009/0036763 A1 2/2009 Brauker et al.
2009/0036915 A1 2/2009 Karbowniczek et al.
2009/0043181 A1 2/2009 Brauker et al.
2009/0043182 A1 2/2009 Brauker et al.
2009/0043525 A1 2/2009 Brauker et al.
2009/0043541 A1 2/2009 Brauker et al.
2009/0043542 A1 2/2009 Brauker et al.
2009/0045055 A1 2/2009 Rhodes et al.
2009/0054866 A1 2/2009 Teisen-Simony et al.
2009/0062633 A1 3/2009 Brauker et al.

(56) References Cited

U.S. PATENT DOCUMENTS

| | | | |
|---|---|---|---|
| 2009/0062635 | A1 | 3/2009 | Brauker et al. |
| 2009/0069658 | A1 | 3/2009 | Say et al. |
| 2009/0069750 | A1 | 3/2009 | Schraga |
| 2009/0076356 | A1 | 3/2009 | Simpson et al. |
| 2009/0076359 | A1 | 3/2009 | Peyser |
| 2009/0076360 | A1 | 3/2009 | Brister et al. |
| 2009/0076361 | A1 | 3/2009 | Kamath et al. |
| 2009/0082693 | A1 | 3/2009 | Stafford |
| 2009/0088614 | A1 | 4/2009 | Taub |
| 2009/0088787 | A1 | 4/2009 | Koike et al. |
| 2009/0102678 | A1 | 4/2009 | Mazza et al. |
| 2009/0105569 | A1 | 4/2009 | Stafford |
| 2009/0124877 | A1 | 5/2009 | Shariati et al. |
| 2009/0124878 | A1 | 5/2009 | Goode et al. |
| 2009/0124879 | A1 | 5/2009 | Brister et al. |
| 2009/0124964 | A1 | 5/2009 | Leach et al. |
| 2009/0124979 | A1 | 5/2009 | Raymond et al. |
| 2009/0131776 | A1 | 5/2009 | Simpson et al. |
| 2009/0131777 | A1 | 5/2009 | Simpson et al. |
| 2009/0131860 | A1 | 5/2009 | Nielsen |
| 2009/0137886 | A1 | 5/2009 | Shariati et al. |
| 2009/0137887 | A1 | 5/2009 | Shariati et al. |
| 2009/0143659 | A1 | 6/2009 | Li et al. |
| 2009/0143660 | A1 | 6/2009 | Brister et al. |
| 2009/0156919 | A1 | 6/2009 | Brister et al. |
| 2009/0156924 | A1 | 6/2009 | Shariati et al. |
| 2009/0163790 | A1 | 6/2009 | Brister et al. |
| 2009/0163791 | A1 | 6/2009 | Brister et al. |
| 2009/0171182 | A1 | 7/2009 | Stafford |
| 2009/0178459 | A1 | 7/2009 | Li et al. |
| 2009/0182217 | A1 | 7/2009 | Li et al. |
| 2009/0192366 | A1 | 7/2009 | Mensinger et al. |
| 2009/0192380 | A1 | 7/2009 | Shariati et al. |
| 2009/0192722 | A1 | 7/2009 | Shariati et al. |
| 2009/0192724 | A1 | 7/2009 | Brauker et al. |
| 2009/0192745 | A1 | 7/2009 | Kamath et al. |
| 2009/0192751 | A1 | 7/2009 | Kamath et al. |
| 2009/0198215 | A1 | 8/2009 | Chong et al. |
| 2009/0203981 | A1 | 8/2009 | Brauker et al. |
| 2009/0204341 | A1 | 8/2009 | Brauker et al. |
| 2009/0212766 | A1 | 8/2009 | Olson et al. |
| 2009/0216103 | A1 | 8/2009 | Brister et al. |
| 2009/0240120 | A1 | 9/2009 | Mensinger et al. |
| 2009/0240128 | A1 | 9/2009 | Mensinger et al. |
| 2009/0240193 | A1 | 9/2009 | Mensinger et al. |
| 2009/0242399 | A1 | 10/2009 | Kamath et al. |
| 2009/0242425 | A1 | 10/2009 | Kamath et al. |
| 2009/0247855 | A1 | 10/2009 | Boock et al. |
| 2009/0247856 | A1 | 10/2009 | Boock et al. |
| 2009/0259118 | A1 | 10/2009 | Feldman et al. |
| 2009/0259201 | A1 | 10/2009 | Hwang et al. |
| 2009/0259202 | A1 | 10/2009 | Leeflang et al. |
| 2009/0270765 | A1 | 10/2009 | Ghesquire et al. |
| 2009/0287073 | A1 | 11/2009 | Boock et al. |
| 2009/0287074 | A1 | 11/2009 | Shults et al. |
| 2009/0292184 | A1 | 11/2009 | Funderburk et al. |
| 2009/0292185 | A1 | 11/2009 | Funderburk et al. |
| 2009/0299155 | A1 | 12/2009 | Yang et al. |
| 2009/0299156 | A1 | 12/2009 | Simpson et al. |
| 2009/0299162 | A1 | 12/2009 | Brauker et al. |
| 2009/0299167 | A1 | 12/2009 | Seymour |
| 2009/0299276 | A1 | 12/2009 | Brauker et al. |
| 2010/0004597 | A1 | 1/2010 | Gryn et al. |
| 2010/0010324 | A1 | 1/2010 | Brauker et al. |
| 2010/0010331 | A1 | 1/2010 | Brauker et al. |
| 2010/0010332 | A1 | 1/2010 | Brauker et al. |
| 2010/0016687 | A1 | 1/2010 | Brauker et al. |
| 2010/0016698 | A1 | 1/2010 | Rasdal et al. |
| 2010/0022855 | A1 | 1/2010 | Brauker et al. |
| 2010/0030038 | A1 | 2/2010 | Brauker et al. |
| 2010/0030053 | A1 | 2/2010 | Goode, Jr. et al. |
| 2010/0030484 | A1 | 2/2010 | Brauker et al. |
| 2010/0030485 | A1 | 2/2010 | Brauker et al. |
| 2010/0036215 | A1 | 2/2010 | Goode, Jr. et al. |
| 2010/0036216 | A1 | 2/2010 | Goode, Jr. et al. |
| 2010/0036222 | A1 | 2/2010 | Goode, Jr. et al. |
| 2010/0036223 | A1 | 2/2010 | Goode, Jr. et al. |
| 2010/0036225 | A1 | 2/2010 | Goode, Jr. et al. |
| 2010/0036281 | A1 | 2/2010 | Doi |
| 2010/0041971 | A1 | 2/2010 | Goode, Jr. et al. |
| 2010/0045465 | A1 | 2/2010 | Brauker et al. |
| 2010/0049014 | A1 | 2/2010 | Funderburk et al. |
| 2010/0049024 | A1 | 2/2010 | Saint et al. |
| 2010/0063373 | A1 | 3/2010 | Kamath et al. |
| 2010/0069728 | A1 | 3/2010 | Funderburk et al. |
| 2010/0076283 | A1 | 3/2010 | Simpson et al. |
| 2010/0081908 | A1 | 4/2010 | Dobbles et al. |
| 2010/0081910 | A1 | 4/2010 | Brister et al. |
| 2010/0087724 | A1 | 4/2010 | Brauker et al. |
| 2010/0096259 | A1 | 4/2010 | Zhang et al. |
| 2010/0099970 | A1 | 4/2010 | Shults et al. |
| 2010/0099971 | A1 | 4/2010 | Shults et al. |
| 2010/0100113 | A1 | 4/2010 | Lio et al. |
| 2010/0106088 | A1 | 4/2010 | Yodfat et al. |
| 2010/0113897 | A1 | 5/2010 | Brenneman et al. |
| 2010/0119693 | A1 | 5/2010 | Tapsak et al. |
| 2010/0121169 | A1 | 5/2010 | Petisce et al. |
| 2010/0168677 | A1 | 7/2010 | Gabriel et al. |
| 2010/0174157 | A1 | 7/2010 | Brister et al. |
| 2010/0174158 | A1 | 7/2010 | Kamath et al. |
| 2010/0174163 | A1 | 7/2010 | Brister et al. |
| 2010/0174164 | A1 | 7/2010 | Brister et al. |
| 2010/0174165 | A1 | 7/2010 | Brister et al. |
| 2010/0174166 | A1 | 7/2010 | Brister et al. |
| 2010/0174167 | A1 | 7/2010 | Kamath et al. |
| 2010/0174168 | A1 | 7/2010 | Goode et al. |
| 2010/0179401 | A1 | 7/2010 | Rasdal et al. |
| 2010/0179402 | A1 | 7/2010 | Goode et al. |
| 2010/0179404 | A1 | 7/2010 | Kamath et al. |
| 2010/0179408 | A1 | 7/2010 | Kamath et al. |
| 2010/0179409 | A1 | 7/2010 | Kamath et al. |
| 2010/0185065 | A1 | 7/2010 | Goode et al. |
| 2010/0185069 | A1 | 7/2010 | Brister et al. |
| 2010/0185070 | A1 | 7/2010 | Brister et al. |
| 2010/0185071 | A1 | 7/2010 | Simpson et al. |
| 2010/0185072 | A1 | 7/2010 | Goode et al. |
| 2010/0185075 | A1 | 7/2010 | Brister et al. |
| 2010/0191082 | A1 | 7/2010 | Brister et al. |
| 2010/0198033 | A1 | 8/2010 | Krulevitch et al. |
| 2010/0198034 | A1 | 8/2010 | Thomas et al. |
| 2010/0198035 | A1 | 8/2010 | Kamath et al. |
| 2010/0198036 | A1 | 8/2010 | Kamath et al. |
| 2010/0204653 | A1 | 8/2010 | Gryn et al. |
| 2010/0212583 | A1 | 8/2010 | Brister et al. |
| 2010/0214104 | A1 | 8/2010 | Goode et al. |
| 2010/0217105 | A1 | 8/2010 | Yodfat et al. |
| 2010/0217557 | A1 | 8/2010 | Kamath et al. |
| 2010/0223013 | A1 | 9/2010 | Kamath et al. |
| 2010/0223022 | A1 | 9/2010 | Kamath et al. |
| 2010/0223023 | A1 | 9/2010 | Kamath et al. |
| 2010/0228109 | A1 | 9/2010 | Kamath et al. |
| 2010/0228497 | A1 | 9/2010 | Kamath et al. |
| 2010/0240975 | A1 | 9/2010 | Goode et al. |
| 2010/0240976 | A1 | 9/2010 | Goode et al. |
| 2010/0261987 | A1 | 10/2010 | Kamath et al. |
| 2010/0262201 | A1 | 10/2010 | He et al. |
| 2010/0274107 | A1 | 10/2010 | Boock et al. |
| 2010/0280341 | A1 | 11/2010 | Boock et al. |
| 2010/0286496 | A1 | 11/2010 | Simpson et al. |
| 2010/0298684 | A1 | 11/2010 | Leach et al. |
| 2010/0324403 | A1 | 12/2010 | Brister et al. |
| 2010/0331642 | A1 | 12/2010 | Bruce et al. |
| 2010/0331644 | A1 | 12/2010 | Neale et al. |
| 2010/0331647 | A1 | 12/2010 | Shah et al. |
| 2010/0331648 | A1 | 12/2010 | Kamath et al. |
| 2010/0331656 | A1 | 12/2010 | Mensinger et al. |
| 2010/0331657 | A1 | 12/2010 | Mensinger et al. |
| 2011/0004085 | A1 | 1/2011 | Mensinger et al. |
| 2011/0009727 | A1 | 1/2011 | Mensinger et al. |
| 2011/0024043 | A1 | 2/2011 | Boock et al. |
| 2011/0024307 | A1 | 2/2011 | Simpson et al. |
| 2011/0027127 | A1 | 2/2011 | Simpson et al. |
| 2011/0027453 | A1 | 2/2011 | Boock et al. |
| 2011/0027458 | A1 | 2/2011 | Boock et al. |

(56) References Cited

U.S. PATENT DOCUMENTS

| | | | | |
|---|---|---|---|---|
| 2011/0028815 | A1 | 2/2011 | Simpson et al. | |
| 2011/0028816 | A1 | 2/2011 | Simpson et al. | |
| 2011/0040256 | A1 | 2/2011 | Bobroff et al. | |
| 2011/0040263 | A1 | 2/2011 | Hordum et al. | |
| 2011/0046456 | A1 | 2/2011 | Hordum et al. | |
| 2011/0046467 | A1 | 2/2011 | Simpson et al. | |
| 2011/0077490 | A1 | 3/2011 | Simpson et al. | |
| 2011/0118579 | A1 | 5/2011 | Goode et al. | |
| 2011/0118580 | A1 | 5/2011 | Goode et al. | |
| 2011/0124992 | A1 | 5/2011 | Brauker et al. | |
| 2011/0124997 | A1 | 5/2011 | Goode et al. | |
| 2011/0125410 | A1 | 5/2011 | Goode et al. | |
| 2011/0130970 | A1 | 6/2011 | Goode et al. | |
| 2011/0130971 | A1 | 6/2011 | Goode et al. | |
| 2011/0130998 | A1 | 6/2011 | Goode et al. | |
| 2011/0137257 | A1 | 6/2011 | Gyrn et al. | |
| 2011/0144465 | A1 | 6/2011 | Shults et al. | |
| 2011/0178378 | A1 | 7/2011 | Brister et al. | |
| 2011/0178461 | A1 | 7/2011 | Chong et al. | |
| 2011/0190614 | A1 | 8/2011 | Brister et al. | |
| 2011/0191044 | A1 | 8/2011 | Stafford | |
| 2011/0201910 | A1 | 8/2011 | Rasdal et al. | |
| 2011/0201911 | A1 | 8/2011 | Johnson et al. | |
| 2011/0218414 | A1 | 9/2011 | Kamath et al. | |
| 2011/0231107 | A1 | 9/2011 | Brauker et al. | |
| 2011/0231140 | A1 | 9/2011 | Goode et al. | |
| 2011/0231141 | A1 | 9/2011 | Goode et al. | |
| 2011/0231142 | A1 | 9/2011 | Goode et al. | |
| 2011/0253533 | A1 | 10/2011 | Shults et al. | |
| 2011/0257521 | A1 | 10/2011 | Fraden | |
| 2011/0257895 | A1 | 10/2011 | Brauker et al. | |
| 2011/0263958 | A1 | 10/2011 | Brauker et al. | |
| 2011/0270062 | A1 | 11/2011 | Goode et al. | |
| 2011/0270158 | A1 | 11/2011 | Brauker et al. | |
| 2011/0275919 | A1 | 11/2011 | Petisce et al. | |
| 2011/0290645 | A1 | 12/2011 | Brister et al. | |
| 2011/0313543 | A1 | 12/2011 | Brauker et al. | |
| 2011/0319739 | A1 | 12/2011 | Kamath et al. | |
| 2011/0320130 | A1 | 12/2011 | Valdes et al. | |
| 2012/0035445 | A1 | 2/2012 | Boock et al. | |
| 2012/0040101 | A1 | 2/2012 | Tapsak et al. | |
| 2012/0046534 | A1 | 2/2012 | Simpson et al. | |
| 2012/0078071 | A1 | 3/2012 | Bohm et al. | |
| 2012/0108934 | A1 | 5/2012 | Valdes et al. | |
| 2012/0108983 | A1 | 5/2012 | Banet et al. | |
| 2012/0123385 | A1 | 5/2012 | Edwards et al. | |
| 2012/0190952 | A1 * | 7/2012 | Stafford .............. | A61M 5/1723 600/345 |
| 2012/0296327 | A1 | 11/2012 | Hutchins et al. | |
| 2013/0047981 | A1 | 2/2013 | Bacon | |
| 2016/0151569 | A1 * | 6/2016 | Stafford .............. | A61M 5/1723 600/365 |
| 2019/0298921 | A1 * | 10/2019 | Stafford ............... | A61B 5/6833 |

FOREIGN PATENT DOCUMENTS

| | | | | |
|---|---|---|---|---|
| EP | 1630898 | | 3/2006 | |
| EP | 0987982 | | 1/2007 | |
| EP | 2060284 | | 5/2009 | |
| EP | 2201969 | | 6/2010 | |
| EP | 2327362 | | 6/2011 | |
| EP | 2335587 | | 6/2011 | |
| JP | 11-506629 | | 6/1999 | |
| JP | 2003-516011 | | 5/2003 | |
| JP | 2004-520103 | | 7/2004 | |
| JP | 2004-520898 | | 7/2004 | |
| WO | WO-1996/039977 | | 5/1996 | |
| WO | WO-1997/021457 | | 6/1997 | |
| WO | WO-1998/056293 | | 12/1998 | |
| WO | WO-1999/033504 | | 7/1999 | |
| WO | WO-2002/050534 | | 6/2002 | |
| WO | WO-2002/058537 | | 8/2002 | |
| WO | WO-2003/028784 | | 4/2003 | |
| WO | WO-2003/073936 | | 9/2003 | |
| WO | WO-2003/076893 | | 9/2003 | |
| WO | WO-2003/082091 | | 10/2003 | |
| WO | WO-2004/054445 | | 7/2004 | |
| WO | WO-2004/060436 | | 7/2004 | |
| WO | WO-2004/061420 | | 7/2004 | |
| WO | WO-2005/084534 | | 9/2005 | |
| WO | WO-2005/089103 | | 9/2005 | |
| WO | WO-2006/042811 | | 4/2006 | |
| WO | WO-2006/108809 | | 10/2006 | |
| WO | WO-2006120253 | A2 * | 11/2006 | ........ A61M 5/14248 |
| WO | WO-2007/016399 | | 2/2007 | |
| WO | WO-2007/027788 | | 3/2007 | |
| WO | WO-2007/041069 | | 4/2007 | |
| WO | WO-2007/041070 | | 4/2007 | |
| WO | WO-2007/041248 | | 4/2007 | |
| WO | WO-2007/120363 | | 10/2007 | |
| WO | WO-2007/140783 | | 12/2007 | |
| WO | WO-2007/143225 | | 12/2007 | |
| WO | WO-2008/031106 | | 3/2008 | |
| WO | WO-2008/031110 | | 3/2008 | |
| WO | WO-2008/039944 | | 4/2008 | |
| WO | WO-2008/051920 | | 5/2008 | |
| WO | WO-2008/051924 | | 5/2008 | |
| WO | WO2008/065646 | | 6/2008 | |
| WO | WO2008/133702 | | 11/2008 | |
| WO | WO-2008/150917 | | 12/2008 | |
| WO | WO2009/062675 | | 5/2009 | |
| WO | WO2010/112521 | | 10/2010 | |
| WO | WO-20111002815 | | 1/2011 | |

OTHER PUBLICATIONS

US Patent Application No. 2006/0276771 A1, Galley et al., published Dec. 7, 2006; 17 pages, Anlage TW 11 D2, Taylor Wessing, Statement of Defence in *Abbott* v. *Dexcom*, Opposition to EP 3782539.

US Patent Application No. 2008/0119710 A1, Reggiardo et al., published May 22, 2008; 12 pages, Anlage TW 11 D4, Taylor Wessing, Statement of Defence in *Abbott* v. *Dexcom*, Opposition to EP 3782539.

Gunasingham, et al., "Electrochemically Modulated Optrode for Glucose", Biosensors & Bioelectronics, vol. 7, 1992, pp. 353-359.

Ikeda, T., et al., "Artificial Pancreas—Investigation of the Stability of Glucose Sensors Using a Telemetry System", Jpn. J. Artif. Organs, vol. 19, No. 2, 1990, 889-892.

Minimed Technologies, "Tape Tips and Other Infusion Site Information", 1995.

Alcock & Turner, "Continuous analyte monitoring to aid clinical practice," IEEE Engineering in Medicine & BioloXY Magazine, 13:319-25 (1994).

Armour et al., "Application of Chronic Intravascular Blood Glucose Sensor in Dogs," Diabetes, vol. 39, pp. 1519-1526, Dec. 1990.

Aussedat, B., et al., "A User-Friendly Method for Calibrating a Subcutaneous Glucose Sensor-Based Hypoglycemic Alarm", Biosensors & Bioelectronics, vol. 12, No. 11, 1997, pp. 1061-1071.

Bennion, N., et al., "Alternate Site Glucose Testing: A Crossover Design", Diabetes Technology & Therapeutics vol. 4 No. 1, 2002, pp. 25-33.

Bindra, D.S. et al., "Design and in Vitro Studies of a Needle-Type Glucose Sensor for Subcutaneous Monitoring", Anal. Chem., 63(17):1692-1696 (Sep. 1, 1991).

Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE vol. 4624, 2002, pp. 1-10.

Bobbioni-Harsch, E. et al., "Lifespan of subcutaneous glucose sensors and their performances during dynamic glycaemia changes in rats," J. Biomed. Eng. 15:457-463 (1993).

Brooks, S. L., et al., "Development of an On-Line Glucose Sensor for Fermentation Monitoring", Biosensors, vol. 3, 1987/88, pp. 45-56.

Cass, A.E.G. et al., "Ferrocene-Mediated Enzyme Electrode for Amperometric Determination of Glucose", Anal. Chem., 56(4):667-671 (Apr. 1984).

(56) References Cited

OTHER PUBLICATIONS

Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.
Feldman, B., et al., "A Continuous Glucose Sensor Based on Wired EnzymeTM Technology—Results from a 3-Day Trial in Patients with Type 1 Diabetes", Diabetes Technology & Therapeutics, vol. 5, No. 5, 2003, pp. 769-779.
Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.
Gregg, B. A. et al., "Cross-Linked Redox Gels Containing Glucose Oxidase for Amperometric Biosensor Applications," Analytical Chemistry, 62(3):258-263 (Feb. 1, 1990).
Harrison, DJ. et al., "Characterization of Perfluorosulfonic Acid Polymer Coated Enzyme Electrodes and a Miniaturized Integrated Potentiostat for Glucose Analysis in Whole Blood", Anal. Chem., 60 (19):2002-2007 (Oct. 1, 1988).
Heller, A., "Electrical Connection of Enzyme Redox Centers to Electrodes," J. Phys. Chern., 96 (9):3579-3587 (1992).
Isermann, R., "Supervision, Fault-Detection and Fault-Diagnosis Methods—An Introduction", Control Engineering Practice vol. 5 No.5, 1997, pp. 639-652.
Isermann, R., et al., "Trends in the Application of Model-Based Fault Detection and Diagnosis of Technical Processes", Control Engineering Practice vol. 5 No. 5, 1997, pp. 709-719.
Johnson, K., et al., "In vivo evaluation of an electroenzymatic glucose sensor implanted in subcutaneous tissue", Biosensors and Bioelectronics, 1992, vol. 7, pp. 709-714.
Johnson, P. C., "Peripheral Circulation", John Wiley & Sons, 1978, pp. 198.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", Diabetes Care, vol. 24, No. 7, 2001, pp. 1303-1304.
Kaplan, S. M., "Wiley Electrical and Electronics Engineering Dictionary", IEEE Press, 2004, pp. 141, 142,548,549.
Lortz, J., et al., "What is Bluetooth? We Explain The Newest Short-Range Connectivity Technology", Smart Computing Learning Series, Wireless Computing, vol. 8, Issue 5, 2002, pp. 72-74.
Maidan, R. et al., "Elimination of Electrooxidizable Interferant-Produced Currents in Amperometric Biosensors," Analytical Chemistry, 64(23):2889-2896 (Dec. 1, 1992).
Malin, S. F., et al., "Noninvasive Prediction of Glucose by Near-Infrared Diffuse Reflectance Spectoscopy", Clinical Chemistry, vol. 45, No. 9, 1999, pp. 1651-1658.
Mastrototaro, J.J. et al., "An Electroenzymatic Glucose Sensor Fabricated on a Flexible Substrate", Sensors and Biosensors B Chemical, B5: 139-144 (1991).
McGarraugh, G., et al., "Glucose Measurements Using Blood Extracted from the Forearm and the Finger", TheraSense, Inc., 2001, 16 Pages.
McGarraugh, G., et al., "Physiological Influences on Off-Finger Glucose Testing", Diabetes Technology & Therapeutics, vol. 3, No. 3, 2001, pp. 367-376.
McKean, B. et al. "A Telemetry-Instrumentation System for Chronically Implanted Glucose and Oxygen Sensors," IEEE Transactions on Biomedical Engineering, vol. 35, No. 7, (Jul. 1988), pp. 526-532.
Moatti-Sirat, D. et al., "Towards continuous glucose monitoring: in vivo evaluation of a miniaturized glucose sensor implanted for several days in rat subcutaneous tissue," Diabetolocia, 35(3) (1 page—Abstract only) (Mar. 1992).
Ohara, T. J. et al., "Glucose Electrodes Based on Cross-Linked $[Os(bpy)_2Cl]^{+/2+}$ Complexed Poly(Ivinylimadazole) Films," Analytical Chemistry, 65(23):3512-3516 (Dec. 1, 1993).
Pickup, J., et al., "Implantable Glucose Sensors: Choosing the Appropriate Sensing Strategy", Biosensors, vol. 3, 1987/88, pp. 335-346.
Pickup, J., et al., "In Vivo Molecular Sensing in Diabetes Mellitus: An Implantable Glucose Sensor with Direct Electron Transfer", Diabetologia, vol. 32, 1989, pp. 213-217.
Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268-2272.
Poitout, V. et al., "In vitro and in vivo evaluation in dogs of a miniaturized glucose sensor," ASAIO Transactions, 37(3) (1 page—Abstract only) (Jul.-Sep. 1991).
Quinn, C. P., et al., "Kinetics of Glucose Delivery to Subcutaneous Tissue in Rats Measured with 0.3-mm Amperometric Microsensors", The American Physiological Society, 1995, E155-E161.
Reach, G. et al., "Can Continuous Glucose Monitoring Be Used for the Treatment of Diabetes?" Analytical Chemistry, 64(6):381-386 (Mar. 15, 1992).
Rebrin, K. et al., "Automated Feedback Control of Subcutaneous Glucose Concentration in Diabetic Dogs", Diabetologia, 32(8):573-576 (Aug. 1989).
Roe, J. N., et al., "Bloodless Glucose Measurements", Critical Review in Therapeutic Drug Carrier Systems, vol. 15, Issue 3, 1998, pp. 199-241.
Sakakida, M. et al., "Ferrocene-mediate needle-type glucose sensor covered with newly designed biocompatible membrane," Sensors and Actuators B, 13-14:319-322 (1993).
Sakakida, M., et al., "Development offerrocene-mediated needle-type glucose sensor as a measure of true subcutaneous tissue glucose concentrations", Artif Organs Today. 1992, vol. 2, No. 2, pp. 145-458.
Salehi, C., et al., "A Telemetry-Instrumentation System for Long-Term Implantable Glucose and Oxygen Sensors", Analytical Letters, vol. 29, No. 13, 1996, pp. 2289-2308.
Schmidt, F. J., et al., "Calibration of a Wearable Glucose Sensor", The International Journal of Artificial Organs, vol. 15, No. 1, 1992, pp. 55-61.
Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.
Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.
Shichiri, M. et al., "Glycaemic Control in Pancrearetomized Dogs with a Wearable Artificial Endocrine Pancreas", Diabetologia, 24(3):179-184 (Mar. 1983).
Shichiri, M. et al., "Telemetry Glucose Monitoring Device with Needle-type Glucose Sensor: A Useful Tool for Blood Glucose Monitoring in Diabetic Individuals," Diabetes Care, vol. 9, No. 3 (May-Jun. 1986), pp. 298-301.
Shichiri, M., et al., "In vivo characteristics of needle-type glucose sensor—Measurement of subcutaneous glucose concentrations in human volunteers". Hormone and Metabolic Res Suppl. 1988, vol. 20, pp. 17-20.
Shichiri, M., et al., "Membrane Design for Extending the Long-Life of an Implantable Glucose Sensor", Diabetes Nutrition and Metabolism, vol. 2, 1989, pp. 309-313.
Shichiri, M., et al., "Needle-type Glucose Sensor for Wearable Artificial Endocrine Pancreas", Implantable Sensors for Closed-Loop Prosthetic Systems Chapter 15, 1985, pp. 197-210.
Shichiri, M., et al., "Wearable artificial endocrine pancreas with needle-type glucose sensor". The Lancet. Nov. 20, 1982, vol. 2, No. 8308, pp. 1129-1131.
Shults, M., "A Telemetry-Instrumentation System for Monitoring Multiple Subcutaneously Implanted Glucose Sensors," IEEE Transactions on Biomedical Engineering, vol. 41, No. 10 (Oct. 1994), pp. 937-942.
Sternberg, R. et al., "Study and Development of Multilayer Needle-type Enzyme-based Glucose Microsensors," Biosensors, 4:27-40 (1988).

(56) References Cited

OTHER PUBLICATIONS

Thompson, M., et al., "In Vivo Probes: Problems and Perspectives", Clinical Biochemistry, vol. 19, 1986, pp. 255-261.
Turner, A.P.F. et al., "Diabetes Mellitus: Biosensors for Research and Management", Biosensors, 1:85-115 (1985).
Updike, S. et al., "Principles of Long-term Fully Implanted Sensors with Emphasis on Radiotelemetric Monitoring of Blood Glucase from Inside a Subcataneous Foreign Body Capsule (FBC)" in "Biosensors in the Body: Continuous in vivo Monitoring" (John Wiley & Sons, Ltd., 1997) Chapter 4, pp. 117-137.
Velho, G. et al., "Strategies for calibrating a subcutaneous glucose sensor," Biomed Biochim. Acta, 48 (11112):957-964 (1989).
Wilson, G. S. et al., "Progress toward the Development of an Implantable Sensor for Glucose," Clinical Chemistry, 38(9):1613-1617 (1992).
Ye, L. et al., "High Current Density "Wired" Quinoprotein Glucose Dehydrogenase Electroade," Anal. Chem., 65(3):238-241 (Feb. 1, 1993).
Australian Patent Application No. 2007309070, Examination Report mailed Apr. 26, 2012.
Chinese Patent Application No. 200780039416.2 Office Action mailed Apr. 25, 2012.
Chinese Patent Application No. 200780039416.2 Office Action mailed Mar. 30, 2011.
European Patent Application No. EP-07854298.2, Extended European Search Report mailed Mar. 29, 2010.
PCT/US2007/082121 International Search Report and Written Opinion mailed May 9, 2008.
Japanese Patent Application No. 2009-534799 Office Action mailed Feb. 19, 2013.
Japanese Patent Application No. 2009-534799 Office Action mailed Sep. 27, 2011.
Japanese Patent Application No. 2013-169447 Office Action mailed Sep. 2, 2014.
Mexican Patent Application No. MX/a12009/004322 Office Action mailed Sep. 19, 2012.
Mexican Patent Application No. MX/a12009/004322 Office Action mailed Mar. 11, 2013.
Russian Patent Application No. 2009-119430 Office Action mailed Jun. 5, 2011.

* cited by examiner

FLEXIBLE PATCH FOR FLUID DELIVERY AND MONITORING BODY ANALYTES

CROSS-REFERENCE TO RELATED APPLICATIONS

The present application is a continuation of U.S. patent application Ser. No. 16/438,556, filed Jun. 12, 2019, which is a continuation of U.S. patent application Ser. No. 14/989,548, filed Jan. 6, 2016, now U.S. Pat. No. 10,363,363, which is a continuation of U.S. patent application Ser. No. 11/552,065, filed Oct. 23, 2006, now U.S. Pat. No. 9,259,175, all of which are incorporated herein by reference in their entireties for all purposes.

FIELD OF THE INVENTION

The present invention relates to medical devices for monitoring analytes in a living body and delivering fluids thereto, such as monitoring glucose levels and delivering insulin to people with diabetes. More particularly, the invention relates to analyte monitoring and fluid delivery systems integrated into a flexible patch.

BACKGROUND OF THE INVENTION

In recent years, people with diabetes have typically measured their blood glucose level by lancing a finger tip or other body location to draw blood, applying the blood to a disposable test strip in a hand-held meter and allowing the meter and strip to perform an electrochemical test of the blood to determine the current glucose concentration. Such discrete, in vitro testing is typically conducted at least several times per day. Continuous in vivo glucose monitoring devices are currently being developed to replace in vitro devices. Some of these continuous systems employ a disposable, transcutaneous sensor that is inserted into the skin to measure glucose concentrations in interstitial fluid. A portion of the sensor protrudes from the skin and is coupled with a durable controller and transmitter unit that is attached to the skin with adhesive. A wireless handheld unit is used in combination with the skin-mounted transmitter and sensor to receive glucose readings periodically, such as once a minute. Every three, five or seven days, the disposable sensor is removed and replaced with a fresh sensor which is again coupled to the reusable controller and transmitter unit. With this arrangement, a person with diabetes may continuously monitor their glucose level with the handheld unit. Detailed descriptions of such a continuous glucose monitoring system and its use are provided in U.S. Pat. No. 6,175,752, issued to Abbott Diabetes Care, Inc., formerly known as TheraSense, Inc., on Jan. 16, 2001, which is incorporated by reference herein in its entirety.

Portable insulin pumps are widely available and are used by diabetic people to automatically deliver insulin over extended periods of time. Currently available insulin pumps employ a common pumping technology, the syringe pump. In a syringe pump, the plunger of the syringe is advanced by a lead screw that is turned by a precision stepper motor. As the plunger advances, fluid is forced out of the syringe, through a catheter to the patient. Insulin pumps need to be very precise to deliver the relatively small volume of insulin required by a typical diabetic (about 0.1 to about 1.0 cm 3 per day) in a nearly continuous manner. The delivery rate of an insulin pump can also be readily adjusted through a large range to accommodate changing insulin requirements of an individual (e.g., various basal rates and bolus doses) by adjusting the stepping rate of the motor. In addition to the renewable insulin reservoir, lead-screw and stepper motor, an insulin pump includes a battery, a controller and associated electronics, and typically a display and user controls. A typical insulin pump has a footprint about the size of a deck of cards and can be worn under clothing or attached with a belt clip. A disposable infusion set is coupled with the pump to deliver insulin to the person. The infusion set includes a cannula that is inserted through the skin, an adhesive mount to hold the cannula in place and a length of tubing to connect the cannula to the pump.

The continuous glucose monitoring and insulin delivery systems described above include various drawbacks. The rigid, flat mounting surfaces of the skin-mounted transmitters currently being developed can make them uncomfortable to wear. Additionally, since these transmitter units do not conform to the portion of the body they are mounted to, adherence to the skin and the locations on the body available for use can be limited. Currently available insulin pumps are complicated and expensive pieces of equipment costing thousands of dollars. The overall size and weight of the insulin pump and the long length of infusion set tubing can make currently available pumping systems cumbersome to use. Additionally, because of their cost, currently available insulin pumps have an intended period of use of up to two years, which necessitates routine maintenance of the device such as recharging the power supply and refilling with insulin.

Various attempts to significantly miniaturize and combine the monitoring and pumping systems described above while making them more reliable, less complex and less expensive have not been successful. Constraints which hinder such development efforts include the system requirements of sensors, insulin supplies and batteries which require periodic replacement, and the need to reduce risk of infection, increase user comfort and ease of use.

SUMMARY OF THE INVENTION

According to aspects of some embodiments of the present invention, an analyte monitoring and/or fluid delivery system is provided having components integrated into a flexible textile patch. The flexible patch may be configured to be worn on the skin of a person or animal. In one embodiment of the invention, a single, patch-mounted system monitors glucose levels of a diabetic person and may provide appropriate doses of insulin in response to the glucose measurements. According to other aspects of the invention, a handheld user interface may be provided for wirelessly controlling the system and/or receiving information from it.

In some embodiments of the invention, conductive pathways are formed in the fabric of the patch. Components that may be integrated with the flexible patch include, but are not limited to: a power source, controller, transmitter, antenna, temperature and other sensors, fluid pump, infusion set, electrical pathways, switches, controls, electrodes, connectors, resistors and other circuit elements. Such components may be embedded, interwoven or coated on to the flexible patch instead of or in addition to surface mounting.

The flexible patch can be constructed of polyester, nylon, polyurethane, Lycra® or other synthetic or natural fibers. In one embodiment, the patch has elastomeric properties that come from properties of the fibers themselves, or from how the fibers are combined to form patch. The flexible patch may be woven, non-woven, knitted, spun or constructed of a textured film, preferably to form an electro-active fabric. Conductive aspects of the textile may come from fine metal wires, either in the yarn used to make the fabric of the patch or woven into the fabric alongside ordinary textile fibers. Alternatively, the electrical properties of patch 12 may come from inherently conductive polymers or nanocomposites deposited as coatings on the fabric's fibers.

According to aspects of some embodiments of the invention, the flexible patch may be soft, stretchable and breathable to increase patient comfort during use. The fabric of the flexible patch may be rolled, crumpled and folded without damaging its functionality. The flexible patch may also be constructed or coated to be flame resistant, water-resistant, or waterproof.

According to aspects of some embodiments of the invention, portions of a flexible patch system or the entire system itself may be disposable, for instance after a predetermined period of use and/or after a particular consumable, such as an insulin supply, is exhausted. For example, just an analyte sensor, an infusion set, and a mounting adhesive may be disposable, while the rest of the flexible patch system is reusable. In such an arrangement, an insulin or other fluid reservoir may be refillable, and/or may comprise a removable cartridge. A portion of electronic circuitry and/or fluid pump may also be removed and reused with a new flexible patch while the remainder of the used patch is discarded. Alternatively, a flexible patch monitoring and fluid delivery system may be constructed inexpensively enough, according to aspects of the present invention, so that the entire system can be disposed of and replaced periodically. Such arrangements would have the advantage of lowering the fixed and recurring costs associated with the use of a monitoring and/or fluid delivery system.

Various analytes may be monitored using aspects of the present invention. These analytes may include, but are not limited to, lactate, acetyl choline, amylase, bilirubin, cholesterol, chorionic gonadotropin, creatine kinase (e.g., CK-MB), creatine, DNA, fructosamine, glucose, glutamine, growth hormones, hematocrit, hemoglobin (e.g. HbA1c), hormones, ketones, lactate, oxygen, peroxide, prostate-specific antigen, prothrombin, RNA, thyroid stimulating hormone, and troponin, in samples of body fluid. Monitoring systems may also be configured to determine the concentration of drugs, such as, for example, antibiotics (e.g., gentamicin, vancomycin, and the like), digitoxin, digoxin, drugs of abuse, theophylline, warfarin and the like. Such analytes may be monitored in blood, interstitial fluid and other bodily fluids. Fluids that can be delivered include but are not limited to insulin and other medicines.

BRIEF DESCRIPTION OF THE DRAWINGS

Each of the figures diagrammatically illustrates aspects of the invention. Of these.

Variation of the invention from that shown in the figures is contemplated.

DETAILED DESCRIPTION

The following description focuses on one variation of the present invention. The variation of the invention is to be taken as a non-limiting example. It is to be understood that the invention is not limited to particular variation(s) set forth and may, of course, vary. Changes may be made to the invention described and equivalents may be substituted (both presently known and future-developed) without departing from the true spirit and scope of the invention. In addition, modifications may be made to adapt a particular situation, material, composition of matter, process, process act(s) or step(s) to the objective(s), spirit or scope of the present invention.

Figure 1:
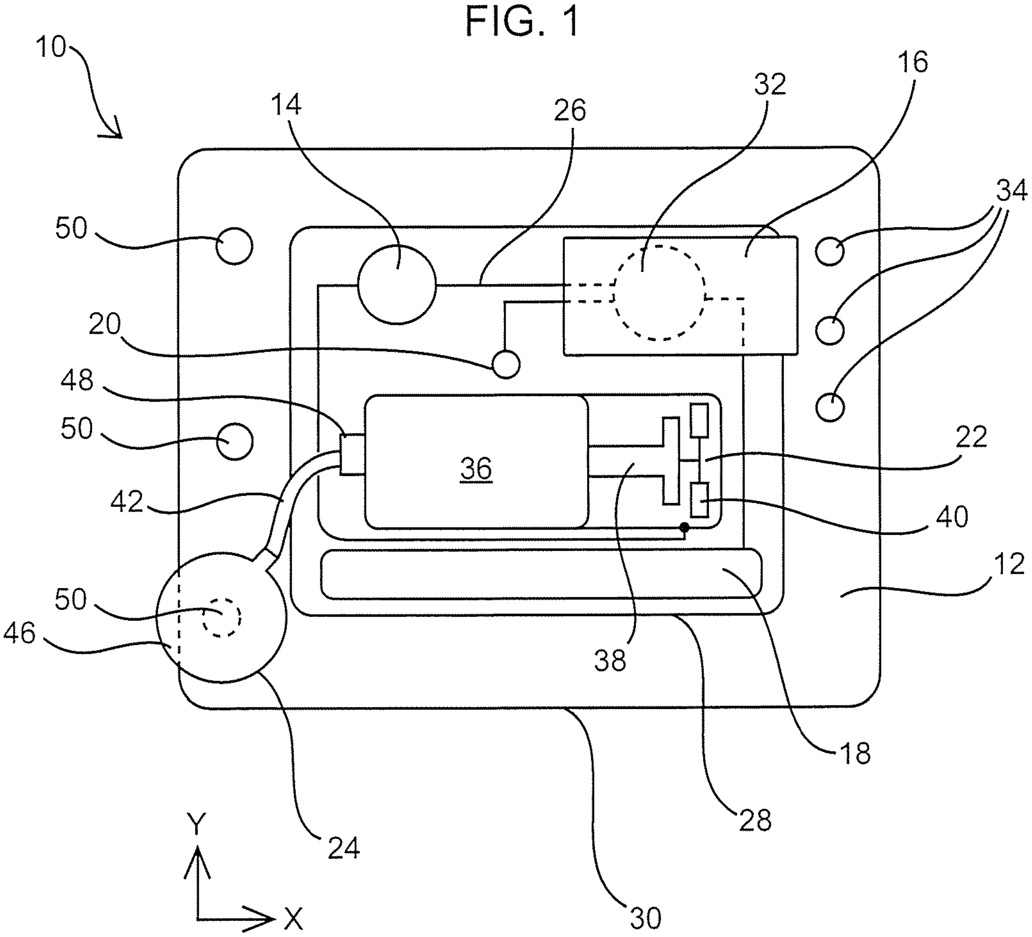
FIG. 1 is a plan view showing an exemplary embodiment of a flexible patch system constructed according to aspects of the present invention.
Figure 2:
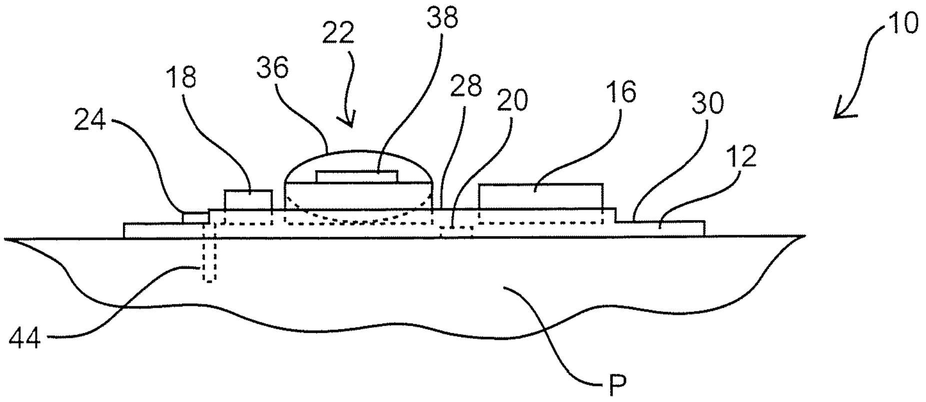
FIG. 2 is a side view of the system of FIG. 1 shown mounted on a patient P.

FIG. 1 shows a top view of an exemplary embodiment of a combined fluid delivery and analyte monitoring system 10 constructed according to some aspects of the present invention, while FIG. 2 shows an elevational end view of system 10 mounted on the skin of patient P. Flexible fabric patch 12 forms the base of system 10. Flexible patch 12 may be provided with an adhesive on a bottom surface to secure patch 12 to the skin of the patient during use. Various components may be attached to or integrated into flexible patch 12, such as power source 14, controller and transmitter module 16, antenna 18, temperature sensor 20, fluid pump 22 and infusion set 24. Electrical pathways 26 may be integrated into flexible patch 12 for interconnecting components of system 10.

Flexible patch 12 may be provided with a thicker area 28, generally towards its center, to afford sufficient support for mounting components. In one embodiment, central area 28 is about 1 mm thick. A peripheral area 30 of flexible patch 12 may be made thinner to promote attachment and adhesion to the skin, particularly as the skin moves and flexes.

Power source 14 may be one or more solar cells, disposable or rechargeable batteries or device, an electrochemical device generating power from an analyte of the patient, and/or other power source suitable for satisfying the power requirements of the components located on flexible patch 12. Such power sources may be directly integrated into flexible patch 12, or removably inserted into a holder attached to patch 12. Power source 14 may itself be flexible by constructing a battery from one or more layers of paper or fabric. Such a paper or fabric battery can convert chemical energy directly into electricity by oxidizing metal on one side of the layer and allowing an oxide to be reduced on the other side when the battery is connected. The metal may be zinc, aluminum, nickel or other metals, the oxide can be manganese oxide, or other oxides, and the paper or fabric layer can contain an electrolyte. Such flexible batteries are currently being developed by companies such as Enfucell Ltd. of Espoo, Finland (www.enfucell.com). Flexible patch 12 itself may comprise one or more layers that can be used to form a flexible battery. Such an arrangement can reduce the need for electrical connectors for the battery, thereby contributing to making the overall system 10 smaller, softer, more conforming to the user and more comfortable to wear.

Circuitry for controller and transmitter 16 may be directly integrated into flexible patch 12. Alternatively, controller and transmitter 16 can be constructed using traditional electronic component assembly techniques then physically and electronically attached to patch 12. Such attachment of module 16 can be permanent or removable. Permanent attachment can be achieved by soldering electrical leads of module 16 to electrical leads on patch 12. Removable attachment of module 16 can be achieved with a traditional electrical connector or with a snap type fitting 32 having electrical pathways interconnecting module 16 to patch 12. Module 16 is preferably powered by power source 14, but may include its own power source in addition to or instead of power source 14.

Antenna 18 preferably is at least somewhat flexible to provide enhanced fit and comfort of patch 12. Antenna 18 can be a separate element physically and electrically coupled with patch 12, but preferably is formed by a conductive layer or layers of patch 12. Antenna 18 is electrically connected to controller and transmitter module 16 to transmit radio frequency (RF) signals such as analyte readings therefrom to an external device, such as a handheld user interface. If module 16 is configured to receive information as well, antenna 18 can be arranged to both transmit and receive RF signals. An infrared (IR) transmitter or transceiver (not shown) can be utilized in addition to or instead of antenna 18 to wirelessly communicate information between system 10 and an external device. A transducer coil and/or cable connector (not shown) can also be provided for external communications, such as to a computer for running diagnostics, or uploading or downloading information.

Flexible patch 12 may be provided with one or more sensor sites 34 for receiving transcutaneous analyte sensors. Multiple sensors can be used simultaneously to provide redundant analyte readings. Alternatively, one sensor may be inserted at a time. After each sensor is used for a predetermined period, such as three, five or seven days each, it can be removed, and a fresh sensor can be inserted at an unused sensor site. Preferably, once all of the sensor sites 34 of a particular patch 12 have been used, patch 12 is removed from the skin and a new patch 12 is applied to a different location on the user's skin. Alternatively, a portion of patch 12 can be reused with a new adhesive portion.

Transcutaneous analyte sensors can be inserted into the user's skin using an automatic introducer or inserter device, such as those described in U.S. patent application Ser. No. 10/703,214, published Jul. 8, 2004 under Publication No. 2004/0133164, now U.S. Pat. No. 7,381,184, incorporated herein by reference in its entirety. An inserted sensor can be electrically connected to controller and transmitter module 16 directly, with external conductors or through internal electrical pathways within flexible patch 12. The sensors may include adhesive mounts, or some type of mounting feature such as one or more snaps, hooks, clamps, pins, clips or other means molded onto or attached to the patch to secure the sensor to flexible patch 12 or to the user's skin during use.

Monitoring and delivery system 10 can also include a temperature sensor 20 for sensing ambient temperature, skin surface temperature or sub-dermal temperature. Ideally, sub-dermal temperature is measured to more accurately calibrate the readings taken by the analyte sensors, since such readings are typically temperature sensitive. However, sub-dermal temperature measurement can be impractical, since this typically necessitates another puncture to the user's skin. Placing a temperature sensor below the surface of the skin can cause discomfort and increased chance of infection. Accordingly, temperature sensor 20 can be mounted to or integrated with the bottom surface of flexible patch 12 to measure the local surface temperature of the skin. From this temperature reading, the higher sub-dermal temperature may be estimated for the depth of penetration associated with sensor 20. In one embodiment, temperature sensor 20 may be connected to controller and transmitter module 16 with internal electrical pathways within flexible patch 12.

A fluid pump 22, such as for delivering insulin or other medicine, can also be located on flexible patch 12. In this exemplary embodiment, fluid pump 22 includes a removable fluid reservoir 36. Reservoir 36 may be a disposable or refillable vial that is replaced by another vial when depleted. Reservoir 36 may be flexible so that it collapses like a balloon when its contents are emptied, or it may include a flexible diaphragm portion. Alternatively, reservoir 36 may be a rigid cylinder with a plunger 38 that forces fluid out when advanced into the reservoir 36. Actuator 40 may be a stepper motor, a shape-memory alloy actuator or other suitable mechanism for advancing plunger 38 or otherwise moving fluid out of reservoir 36. A shape-memory alloy actuator is preferred because of its small size, simplicity and reliability. It's low cost of manufacture also allows pump 22 to be disposable with patch 22 if desired. Details of such a shape-memory alloy driven pump are provided in U.S. patent application Ser. No. 10/683,659, published Jun. 17, 2004 under Publication No. 2004/0115067, now U.S. Pat. No. 6,916,159, incorporated herein by reference in its entirety. Reservoir 36 need not be removable from pump 22 and/or patch 12, particularly if patch 12 is designed to be disposed of after the fluid is depleted.

Pump 22 preferably is powered by power source 14, but may have its own power source. Internal conductive pathways 26 can be used to connect pump 22 with power source 14 and/or controller and transmitter module 16. Pump 22 may be removably or fixedly attached to patch 12. Pump 22 or a pump mounting base may be attached to patch 12 by sandwiching a portion of the patch material between the pump or base and a plate or washer(s) on the opposite side. Alternatively, pump 22 or a mounting base may be attached to patch 12 with an adhesive, fasteners or other suitable means.

In operation, pump 22 can receive control signals from controller and transmitter module 16, causing actuator 40 to push fluid from reservoir 36 into tubing 42 of infusion set 24, through cannula 44 and into the patient. Infusion set 24 may include an adhesive mount 46 for securing the distal end of infusion set 24 to patch 12 or directly to the patient's skin. The proximal end of infusion set 24 may be removably connected to an output port 48 of pump 22. Multiple sites 50 may be provided in the thin region 30 of patch 12 for alternately placing infusion sets 24. An automatic inserter or introducer may be used to insert cannula 44 of infusion set 24 into the patient. Preferably, a single puncture device can be used to insert cannulas 44 and the transcutaneous analyte sensors described above. After a predetermined period of use, typically 3 days, infusion set 24 can be removed by lifting adhesive mount 46, removing cannula 44 from the patient and disconnecting tubing 42 from pump output port 48. A fresh infusion set 24 may then be placed in another one of the sites 50 and connected to pump 22. It may be advantageous to separate infusion set insertion sites 50 as far as possible from sensor insertion sites 34 as shown so that the local effect of the infusion of insulin or other fluid does not interfere with glucose monitoring or other analyte measurement. In one embodiment, infusion sites 50 are spaced about 1 inch apart.

Figure 3:
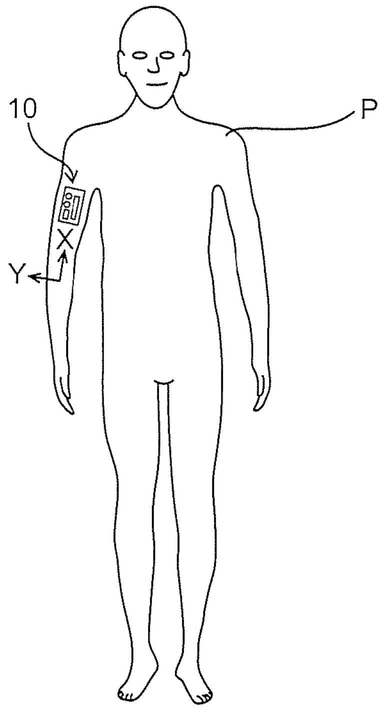
FIG. 3 is a perspective view illustrating the use of the system of FIG. 1 on a person.

In arranging system 10 components on flexible patch 12, the longitudinal axis of components such as controller and transmitter module 16, antenna 18 and pump 22 may be aligned with each other. This allows the overall system to be highly flexible in at least one direction. Since these components may be fairly long and rigid, the exemplary system 10 shown in FIG. 1 is more flexible along the y-axis shown than along the x-axis. With such an arrangement, patch 12 can more compliantly conform to curves of a patient's body when the y-axis is aligned with the direction of the sharpest curve at the application site of patch 12. An example of such an alignment is shown in FIG. 3, where patch 12 is attached to an upper arm of a patient P. As shown, the more compliant y-axis of flexible patch 12 is arranged horizontally to traverse the curve of the arm, while the less compliant x-axis is arranged vertically along the straighter, longitudinal axis of the arm. System 10 may be adhered to other suitable locations of the body, such as the torso, thigh or calf. In this exemplary embodiment, system 10 is about 4 inches long along the x-axis, about 3 inches long along the y-axis and has a maximum thickness of about 0.75 inches at pump 22.

Flexible patch 12 itself can be constructed of polyester, nylon, polyurethane, Lycra® or other synthetic or natural fibers. Preferably, patch 12 has elastomeric properties that come from properties of the fibers themselves, or from how the fibers are combined to form patch 12. Patch 12 can be woven, non-woven, knitted, spun or constructed of a textured film, preferably to form an electro-active fabric. Conductive aspects of the textile can come from fine metal wires, either in the yarn used to make the fabric of patch 12 or woven into the fabric alongside ordinary textile fibers. Alternatively, the electrical properties of patch 12 can come from inherently conductive polymers or nanocomposites deposited as coatings on the fabric's fibers.

As discussed above, various components of system 10 can be woven directly into the fabric of patch 12, including, but not limited to, complex electronic pathways, circuits, controls, electrodes, temperature and other sensors, traces, connectors, resistors, antenna, batteries, switches and other components. Switches and other controls can be incorporated into flexible patch 12 by using a multilayered fabric. For example, three electro-active layers can be used. Two outer conductive layers can surround an inner resistive layer that separates the conductive layers until the layers are momentarily pressed together.

Using fabrics as discussed above, flexible patch 12 can be soft, stretchable and breathable to provide patient comfort during use. Existing fabrics can provide a high moisture vapor transmission rate (MVTR). Such fabrics can be rolled, crumpled and folded without damaging functionality. Patch 12 may also be constructed or coated to be flame resistant, waterproof or water-resistant if desired.

Further information on suitable fabrics, general construction and component integration methods for flexible patch 12 may be obtained from companies currently developing "smart fabrics" or "conductive textiles, such as Textronics (www.textronics.com), Konarka (www.konarka.com), Nanosonic (www.nanosonic.com), Eleksen (www.eleksen.com) and Eeonyx (www.eeonyx.com). For instance, Eeonyx has a proprietary process for coating textiles with inherently conductive polymers based on doped polypyrrole. The company polymerizes the materials in situ—or on the surface of the fabric itself—so the coating material fills interstices in the surface and forms a physical bond with the fibers. See also "Fabrics Get Smart", by Joseph Ogando, Design News, May 15, 2006 (www.designnews.com/article/ca6330247.html), incorporated herein by reference in its entirety.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. An insulin delivery device, comprising:

a patch comprising a bottom surface having an adhesive for securing the patch to a skin surface of a patient, wherein the patch comprises a long axis and a short axis;

a pump for delivering insulin to the patient, wherein the pump is coupled to the patch and is arranged along the long axis of the patch, the pump comprising:

a reservoir configured to store insulin;

a plunger for moving the insulin out of the reservoir;

an actuator configured to advance the plunger through the reservoir; and a cannula in fluid communication with the reservoir and configured to be automatically inserted into an infusion site of the patient to deliver the insulin;

a power source comprising one or more batteries configured to power the pump, wherein the power source is arranged on a first side of the patch and the pump is arranged on an opposing, second side of the patch; and a controller and transmitter module coupled to the patch, wherein the controller and transmitter module comprises an antenna configured to wirelessly communicate with a hand-held user interface device, wherein the antenna comprises a portion extending along a side of the patch in a direction of the long axis of the patch, and wherein the controller and transmitter module is configured to operate the pump to deliver insulin based on signals received from the hand-held user interface device.

2. The device of claim 1, wherein the cannula is configured to extend through an opening at a perimeter of the patch.

3. The device of claim 1, wherein the insulin delivery device is configured to administer insulin based on glucose measurements.

4. The device of claim 1, wherein the patch comprises a rectangular shape.

5. The device of claim 1, wherein the actuator comprises a shape-memory alloy configured to advance the plunger.

6. The device of claim 1, wherein the actuator comprises a motor.

7. The device of claim 1, wherein the power source is arranged on the first side of the patch and the pump is arranged on the opposing, second side of the patch in a direction of the short axis of the patch, wherein the short axis is perpendicular to the long axis in a plane of the patch.

8. The device of claim 7, wherein the patch is more flexible along the short axis than along the long axis.

9. The device of claim 1, wherein the pump has a maximum thickness of 0.75 inches.

10. The device of claim 1, wherein the patch comprises a non-woven material.

11. The device of claim 1, wherein the antenna comprises a conductive layer on the patch.

12. The device of claim 1, wherein the pump is attached to the patch via a mounting base.

13. The device of claim 1, wherein one or more of the pump, the power source, or the controller and transmitter module is integrated into the patch.

14. An insulin delivery system, comprising:
a hand-held user interface device; and
an insulin delivery device in wireless communication with the hand-held user interface device to receive control signals for delivery of insulin, the insulin delivery device comprising:
a patch comprising a bottom surface having an adhesive for securing the patch to a skin surface of a patient, wherein the patch comprises a long axis and a short axis;
a pump for delivering insulin to the patient, wherein the pump is coupled to the patch and is arranged along the long axis of the patch, the pump comprising:
a reservoir configured to store insulin;
a plunger for moving the insulin out of the reservoir;
an actuator configured to advance the plunger through the reservoir; and
a cannula in fluid communication with the reservoir and configured to be automatically inserted into an infusion site of the patient to deliver the insulin;
a power source comprising one or more batteries configured to power the pump, wherein the power source is arranged on a first side of the patch and the pump is arranged on an opposing, second side of the patch; and
a controller and transmitter module coupled to the patch, wherein the controller and transmitter module comprises an antenna configured to wirelessly communicate with the hand-held user interface device, wherein the antenna comprises a portion extending along a side of the patch in a direction of the long axis of the patch, and wherein the controller and transmitter module is configured to operate the pump to deliver insulin based on signals received from the hand-held user interface device.

15. The system of claim 14, wherein the power source is arranged on the first side of the patch and the pump is arranged on the opposing, second side of the patch in a direction of the short axis, wherein the short axis is perpendicular to the long axis in a plane of the patch.

16. The system of claim 15, wherein the patch is more flexible along the short axis than along the long axis.

17. The system of claim 14, wherein the controller and transmitter module of the insulin delivery device is in communication with a transcutaneous glucose sensor.

18. The system of claim 17, wherein the insulin delivery device is configured to administer insulin based on glucose measurements.

* * * * *